United States Patent
Kang et al.

(10) Patent No.: US 11,471,373 B2
(45) Date of Patent: Oct. 18, 2022

(54) MASSAGE CHAIR FOR PERFORMING BRAIN MASSAGE

(71) Applicant: BODYFRIEND CO., LTD., Seoul (KR)

(72) Inventors: Woong Chul Kang, Gyeonggi-do (KR); Soo Hyun Cho, Seoul (KR); Chul Jin Jeon, Seoul (KR); Jeong-Hwan Lim, Seoul (KR)

(73) Assignee: BODYFRIEND CO., LTD., Seoul (KR)

( * ) Notice: Subject to any disclaimer, the term of this patent is extended or adjusted under 35 U.S.C. 154(b) by 240 days.

(21) Appl. No.: 16/756,372

(22) PCT Filed: May 31, 2018

(86) PCT No.: PCT/KR2018/006208
§ 371 (c)(1),
(2) Date: Apr. 15, 2020

(87) PCT Pub. No.: WO2019/088388
PCT Pub. Date: May 9, 2019

(65) Prior Publication Data
US 2020/0330322 A1    Oct. 22, 2020

(30) Foreign Application Priority Data

Nov. 6, 2017   (KR) .......... 10-2017-0146835
Nov. 8, 2017   (KR) .......... 10-2017-0148155

(51) Int. Cl.
*A61H 23/02*     (2006.01)
*A61H 9/00*      (2006.01)
(Continued)

(52) U.S. Cl.
CPC .......... *A61H 23/02* (2013.01); *A61H 9/0007* (2013.01); *A61H 23/006* (2013.01); *A61M 21/02* (2013.01);
(Continued)

(58) Field of Classification Search
None
See application file for complete search history.

(56) References Cited

U.S. PATENT DOCUMENTS 5,553,148 A * 9/1996 Werle .................... H04R 5/023
                                                  381/151
5,807,287 A * 9/1998 Cheng ................ A61H 23/0263
                                                    5/915
(Continued)

FOREIGN PATENT DOCUMENTS

CN     105455999 A    4/2016
CN     105496753 A    4/2016
(Continued)

OTHER PUBLICATIONS

Fahlman, Jason, "binaural beats: benefits of this brainwave entrainment technology", Apr. 17, 2017 (Year: 2017).*

*Primary Examiner* — Samchuan C Yao
*Assistant Examiner* — Savannah L Gabriel
(74) *Attorney, Agent, or Firm* — Novick, Kim & Lee, PLLC; Sang Ho Lee; Hyun Woo Shin

(57) ABSTRACT

Disclosed is a massage device according to one embodiment of the present disclosure. The massage device comprises: a body structure for forming an area to accommodate at least one portion of the body of a user and defining the outer shape of the massage device; a massage module for supplying a massage function to the at least one portion of the body of the user accommodated in the area in the body structure; an input unit for receiving an input of an arbitrary form from the user of the massage device; a display for displaying (Continued)

massage mode screen information which can be selected by the user of the massage device; and a control unit for controlling one more operations of the massage device on the basis of at least a part of the input of an arbitrary form received by the input unit. The massage mode screen information may include: an automatic mode graphic object linked to a function of performing an automatic mode consisting of a predetermined massage pattern and massage time; a manual mode graphic object linked to a function of performing a manual mode to allow a user of the massage device to configure a massage pattern and massage time; and a massage option mode graphic object linked to a function enabling selection of a massage option mode consisting of an additional function that provides convenience to a user of the massage device in addition to a massage operation that applies pressure to at least a part of the body of the user of the massage device.

10 Claims, 19 Drawing Sheets

(51) Int. Cl.
*A61H 23/00* (2006.01)
*A61M 21/02* (2006.01)
*A61M 21/00* (2006.01)

(52) U.S. Cl.
CPC ............... *A61H 2201/0149* (2013.01); *A61H 2201/5005* (2013.01); *A61H 2201/5035* (2013.01); *A61H 2201/5038* (2013.01); *A61H 2201/5043* (2013.01); *A61H 2203/0425* (2013.01); *A61M 2021/0022* (2013.01); *A61M 2021/0027* (2013.01)

(56) References Cited

U.S. PATENT DOCUMENTS

| | | | | |
|---|---|---|---|---|
| 6,123,661 | A * | 9/2000 | Fukushima | A61M 21/00 600/26 |
| 2004/0097851 | A1* | 5/2004 | Inada | A61H 23/0263 601/63 |
| 2006/0247561 | A1* | 11/2006 | Chiu | A61H 23/0236 601/46 |
| 2008/0269652 | A1* | 10/2008 | Reiner | A61M 21/00 601/15 |
| 2009/0227914 | A1* | 9/2009 | Kanaoka | A61H 23/04 601/84 |
| 2010/0249613 | A1* | 9/2010 | Hashimoto | A61M 21/02 600/485 |
| 2015/0169124 | A1 | 6/2015 | Le et al. | |
| 2020/0246579 | A1* | 8/2020 | Cohen | A61H 23/02 |

FOREIGN PATENT DOCUMENTS

| | | | |
|---|---|---|---|
| CN | 106074065 A | 11/2016 | |
| JP | 2004-248974 A | 9/2004 | |
| KR | 10-2013-0027145 A | 3/2013 | |
| KR | 10-1502117 B1 | 3/2015 | |
| KR | 10-2016-0129942 A | 11/2016 | |
| KR | 10-1696556 B1 | 1/2017 | |
| KR | 10-1858927 B1 | 5/2018 | |
| KR | 10-1858928 B1 | 5/2018 | |
| WO | WO-2017175061 A1 * | 10/2017 | A61B 5/024 |

* cited by examiner

MASSAGE CHAIR FOR PERFORMING BRAIN MASSAGE

TECHNICAL FIELD

The present disclosure relates to a massage chair, and more particularly, to a massage chair for performing a brain massage.

BACKGROUND ART

A massage is a medical adjuvant therapy that regulates modulation of a body of a subject, assists in blood circulation, and relieves fatigue of the subject by applying various types of mechanical stimulation to a part of the body, such as kneading, pressing, pulling, tapping, or moving a part of the body of the subject.

For economic and time reasons, an increase in massage demand has led to an increase in demand for a massage device or massage apparatus for providing an artificial massage function. That is, with an increase in demand to relieve fatigue or stress by relaxing tightened muscles through a massage, various time and cost-effective massage devices have been released. Any types of equipment, device, or apparatus that perform a massage through mechanical devices without a separate masseur are referred to as massage devices.

As an example of such a massage device, massage chairs, on which a user may comfortably sit to receive a massage, are mainly used. With an increase in demand for the massage devices, the massage chairs are required to have various functions of relieving fatigue so that a user can rest more comfortably in addition to a function of performing a general massage.

In general, the massage chair may include a massage module configured to directly massage a body of a user and a control mechanism configured to control operation of the massage device. General massage modules may provide artificial stimulation to a user by inflating an airbag toward body parts such as a neck, an arm, a hip, a leg, and a foot by using air pressure, but there may be massage devices having various driving methods. As an example, there may be types of massage devices in which a massage roller is mounted on an elevatable-type rail and is moved in the direction of the rail along a body of a user by rotation of a driving motor, thereby providing stimulation to the user. As another example, there may be types of massage devices in which a massage roller is mounted on a support rotating around a rotation shaft and is rotated along a certain part of a body by rotation of a driving motor, thereby providing stimulation to the user.

Furthermore, as functions implementable by massage devices are added, massage devices, which may provide various types of massage stimulation such as a heating massage function and a low frequency massage function, have been developed. In the case of heating massage devices, a heating wire may be installed in a specific type of panel. In the case of low frequency massage devices, microelectromagnetic waves may be applied to a human body to implement a massage function through stimulation of the electromagnetic waves.

As described above, as the functions implementable by the massage devices are diversified, recently, functions of analyzing a brain wave of a user or checking a biorhythm of the user while performing a massage have also been developed. Along with such attempts, there is a need to develop technology for functions of stimulating a brain wave of a user or controlling a biorhythm of the user through stimulation of the brain wave while the user receives a massage.

US Patent Publication No. US 2008-0269652 discloses a technical feature in which a massage device analyzes a brain wave of a user while performing a massage.

DISCLOSURE

Technical Problem

The present disclosure is directed to providing an optimized brain massage function to a user according to a brain massage mode.

The present disclosure is directed to providing an interface for providing immediacy and convenience of a massage device operation to a user.

Technical Solution

According to one embodiment of the present disclosure, a massage device is provided. The massage device includes a body structure which forms a region for accommodating at least a part of a body of a user and defines an exterior of the massage device, a massage module which provides a massage function to the at least a part of the body of the user accommodated in the region of the body structure, a storage unit which includes a massage pattern information storage unit which stores information about a massage pattern operable by the massage module and an audio information storage unit which stores information about a sound and a binaural beat provided to the user, and a control unit which controls one or more operations of the massage device. The control unit may include a massage pattern analysis unit configured to analyze the information about the massage pattern and an audio optimization unit configured to change volume of the sound and a frequency of the binaural beat over time on the basis of massage pattern analysis information analyzed by the massage pattern analysis unit.

According to one embodiment of the present disclosure, a method performed in a massage device is provided. The method includes receiving a massage mode selection input from a user, determining massage pattern information corresponding to a received massage mode, changing volume of a sound and a frequency of a binaural beat, which are provided to a user, over time on the basis of the determined massage pattern information, and providing an audio output obtained by mixing the sound having the volume changed over time and the binaural beat having the frequency changed over time, together with a massage operation according to a massage pattern corresponding to the received massage mode.

According to one embodiment of the present disclosure, a computer program stored in a computer-readable storage medium including encoded instructions is provided. When the computer program is executed by one or more processors of a computer system, the computer program allows the one or more processors to perform an audio optimization algorithm according to a massage pattern. The audio optimization algorithm may include an operation of receiving a massage mode selection input from a user, an operation of determining massage pattern information corresponding to a received massage mode, an operation of determining to change volume of a sound and a frequency of a binaural beat, which are provided to the user, over time on the basis of the determined massage pattern information, and an operation of determining to provide an audio output obtained by mixing the sound having the volume changed over time and the binaural beat having the frequency changed over time, together with a massage operation according to a massage pattern corresponding to the received massage mode.

Advantageous Effects

According to one embodiment of the present disclosure, an optimized brain massage function can be provided to a user according to a brain massage mode.

According to one embodiment of the present disclosure, an interface for providing immediacy and convenience of a massage device operation can be provided to a user.

DESCRIPTION OF DRAWINGS

Now, various aspects will be described with reference to the accompanying drawings and like reference numerals collectively designate like elements. In the following embodiments, for the purpose of description, various specific details are suggested to provide overall understanding of one or more aspects. However, it is obvious that the aspects may be embodied without the specific details. In other examples, known structures and devices are illustrated in block diagrams in order to easily describe one or more aspects.

BEST MODE OF THE INVENTION

Figure 1:
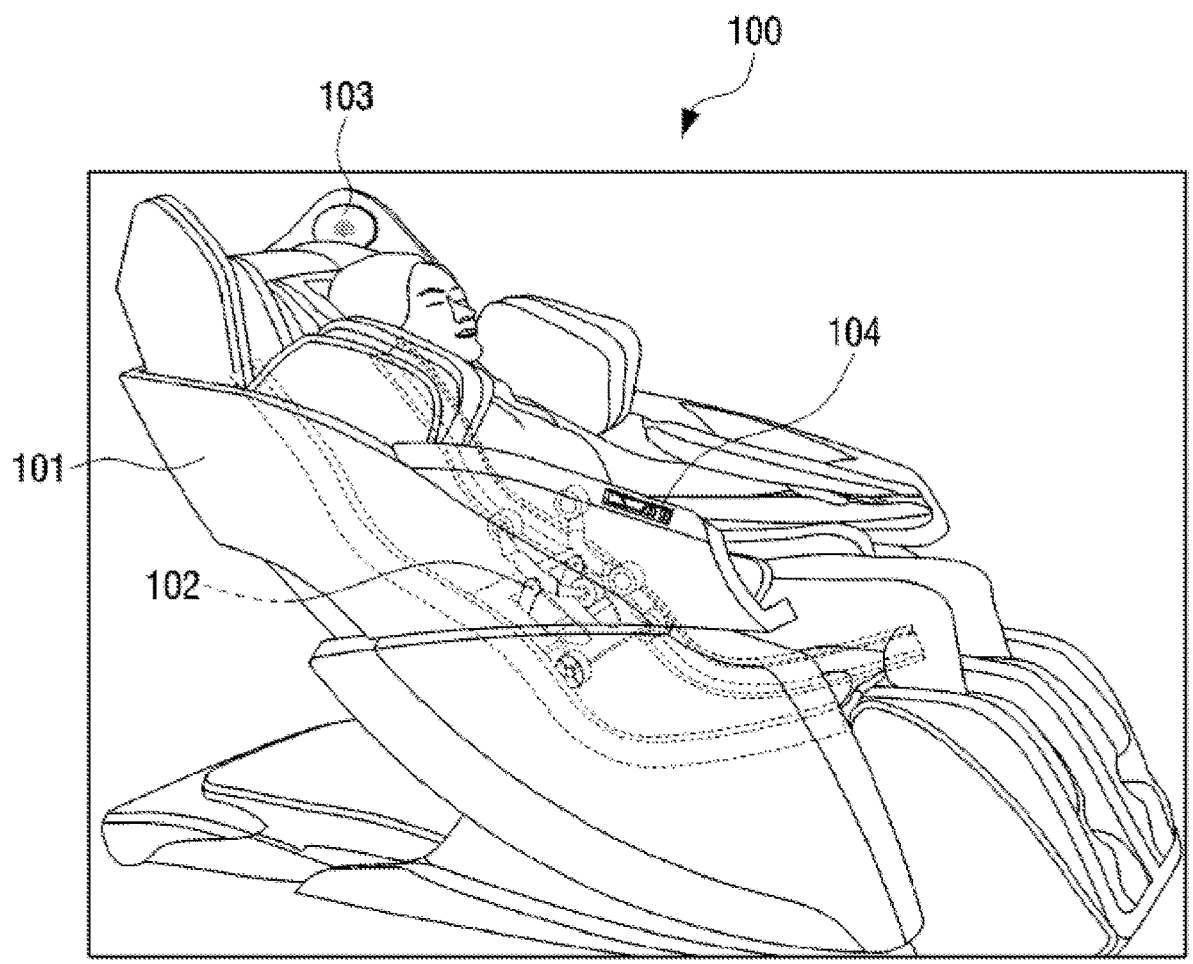
FIG. 1 is an exemplary conceptual diagram illustrating a massage device according to one embodiment of the present disclosure.

A massage device includes a body structure which forms a region for accommodating at least a part of a body of a user and defines an exterior of the massage device, a massage module which provides a massage function to the at least a part of the body of the user accommodated in the region of the body structure, a storage unit which includes a massage pattern information storage unit which stores information about a massage pattern operable by the massage module and an audio information storage unit which stores information about a sound and a binaural beat provided to the user, and a control unit which includes a massage pattern analysis unit configured to analyze the information about the massage pattern to generate massage pattern analysis information and an audio optimization unit configured to change volume of the sound and a frequency of the binaural beat over time on the basis of the massage pattern analysis information.

Modes of the Invention

Various embodiments and/or aspects will be disclosed with reference to the accompanying drawings. In the following description, for the purpose of description, various specific details are disclosed to provide overall understanding of one or more aspects. However, those skilled in the art may understand that the aspect(s) may be embodied without having the specific details. The following description and accompanying drawings thoroughly describe specific exemplary aspects of one or more aspects. However, the aspects are provided for an illustrative purpose, some of various methods in principles of the various aspects may be used, and the descriptions are intended to include all of the aspects and equivalents thereof.

Also, various aspects and features may be implemented by one or more apparatuses, terminals, servers, devices, components, modules, and/or the like. It should also be appreciated and recognized that various systems can include additional apparatuses, terminals, serves, devices, components, modules, and/or the like and/or that the various systems cannot include all of apparatuses, terminals, servers, devices, components, modules, and the like discussed in association with the drawings.

The "embodiment," "example," "aspect," "illustration," and the like used in the present specification may not be interpreted that a described arbitrary aspect or design is better than or more advantageous than other aspects or designs. "Component," "module," "system," "interface," and the like which are terms used below generally mean computer-related entities and mean, for example, hardware, a combination of the hardware and software, or the software.

Further, the term "or" is intended to mean not exclusive "or" but implicational "or." That is, if it is not specifically designated or unclear in the context, "X uses A or B" is intended to refer to one of natural implicational substitutions. In other words, "X uses A or B" may be applied to any case of "X uses A," "X uses B," or "X uses both A and B". Further, it should be understood that the term "and/or" used in the present specification indicates and includes all possible combinations of one or more items among related listed items.

It should be understood that the term "comprise" and/or "comprising" means existence of the corresponding feature and/or element but does not exclude the existence or addition of one or more other features, elements, and a group thereof. In addition, when not separately defined or not clear in terms of the context that a singular form is indicated, it should be construed that the singular form generally means "one or more" in the present specification and the claims.

Further, the terms "information" and "data" used in the present specification may also often be used interchangeably.

The objects and effects of the present disclosure and technical solutions for accomplishing these may be apparent with reference to embodiments to be described below in detail along with the accompanying drawings. In the description of the present disclosure, detailed descriptions of known functions or configurations will be omitted lest it should obscure the subject matter of the present disclosure. The terms as set forth herein are defined in consideration of the functions of the present disclosure and may vary according to the intent of a user and an operator, or customs.

The present disclosure is not limited to the embodiments set forth below and may be embodied in various other forms through a combination between the embodiments within the scope of the appended claims. The present embodiments may be provided to make the present disclosure complete and to enable the skilled person in the art to fully understand the category of the present disclosure. The present disclosure may be defined only by the category described in the appended claims. Thus, the definition may be made based on the entirety of the description of the present specification.

A sound in the present disclosure may include information in any audio form including various types of music such as classical music, jazz music, instrumental music, and pop music, natural sounds such as a water sound and a bird sound, and a binaural beat. In addition, a binaural beat in the present disclosure may refer to audio information in a specific form capable of adjusting a brainwave.

In one embodiment, volume of a sound in the present disclosure may refer to an overall volume of a mixed sound in which a binaural beat and any music are mixed. As another example, volume of a sound in the present disclosure may refer to volume of music (for example, classical music or a natural sound) before being mixed with a binaural beat.

In one embodiment, a frequency of a binaural beat in the present disclosure may refer to a tone-beat frequency, and a unit thereof may be hertz (Hz). As another example, a frequency of a binaural beat in the present disclosure may refer to a tone frequency or a beat frequency.

A massage pattern in the present disclosure may include at least one of (1) a total massage time or a massage time for each flow provided to a user according to a specific mode, (2) a massage type indicating a type of mechanical stimulation provided by a massage module, (3) a massage area or a massage position indicating a position of the massage module, and/or (4) massage intensity indicating intensity of mechanical stimulation provided by the massage module.

A massage device in the present disclosure may refer to equipment, a device, an apparatus, or an instrument which is capable of providing any type of mechanical stimulation to at least a part of a body of a user. In the present disclosure, a massage chair will be described as a representative example of the massage device.

In relation to an additional function of the massage device, any type of sound in which various types of music such as classical music are mixed with a binaural beat may be used for the purpose of improving concentration or relieving stress. In relation to an attempt to provide a healing sound to a user of the massage chair, the massage device may provide an auto massage mode in which a massage pattern is pre-defined for a special purpose of inducing sleep, or convenience. In order to maximize an effect of the auto massage mode, there is also a need for a process of optimizing the healing sound for a massage pattern.

The process of optimizing the healing sound may include a process of changing factors such as volume of the healing sound and a frequency band of a binaural beat according to progress of the massage pattern and mixing the healing sound and the binaural beat so as to output the mixture using the changed factors in an audio output unit of the massage device. As the numbers of auto massage modes and healing music provided by the massage device are increased, an amount of work of manually performing such a process becomes too great, and thus, an algorithm, through which the massage device itself may perform an optimization process, is required.

FIG. 1 is an exemplary conceptual diagram illustrating a massage device 100 according to one embodiment of the present disclosure.

The massage device 100 according to one embodiment of the present disclosure may include a body structure 101 which forms a region for accommodating at least a part of a body of a user and defines an exterior of the massage device, a massage module 102 which provides a massage function to the at least a part of the body of the user accommodated in the region of the body structure, an audio output unit 103 which provides any type of sound to the user, an input unit 104 which receives any type of input from the user, and a display 105 which displays any information about the massage device 100.

The shape and structure of the massage device 100 shown in FIG. 1 are merely examples, and without departing from the scope defined by the scope of the claims of the present disclosure, various types of the massage device 100 may also be included within the scope of the present disclosure.

The body structure 101 may form and define a space having any shape for accommodating the user. The body structure 101 may have an exterior corresponding to a shape of the body of the user. As shown in FIG. 1, for example, the body structure 101 may have a chair or bed shape which may accommodate an entirety or a part of the body of the user. For example, portions of the body structure 101 which come into direct contact with the body of the user may be made of a relatively soft material such as leather, cloth, or cotton in order to increase a wearing sensation of the user. In addition, portions of the body structure 101 which do not come into direct contact with the user may be made of a relatively hard material such as plastic and/or metal in order to promote fixability and stability of the device. A portion of the body structure 101 which comes into contact with the ground may be made of any material for increasing a frictional force or may include any member for increasing a frictional force (for example, a slip prevention pad, a binding portion, a coupling portion, or a contacting portion for increasing a contact force with the ground) in order to enhance fixability with respect to the ground. A movable wheel portion for enhancing mobility of the device may also be provided at a lower end of the body structure 101.

The body structure 101 may include, for example, user-contacting portions with any shapes, which include a headrest which may come into contact with a head of the user, a backrest which may come into contact with a back of the user, a hip seat which may come into contact with a hip of the user, an armrest which may accommodate an arm of the user, a leg massage portion which may accommodate a leg and a foot of the user and provide stimulation to corresponding parts, and the like.

The body structure 101 may include an outer panel having a fixed shape, and the user-contacting portions in contact with the inside of the outer panel may be moved relative to the outer panel in various forms of movement such as a slide movement, a hinge movement, a pivot movement, and/or a tilt movement. The relative movement of each of components in the body structure 101 may be different for each massage mode or massage pattern (for example, the relative movement corresponds to movement by an angle of about 20° with respect to the ground in a first step, movement by an angle of about 40° with respect to the ground in a second step, and movement by an angle of about 170° with respect to the ground in a third step), and thus, a massage effect may be maximized. That is, a posture of receiving a massage may be variably adjusted according to each massage mode or massage pattern, thereby maximizing a massage effect provided to the user.

Additionally, the body structure 101 may include one or more pressure sensors. In this case, a contact area and a contact position between the user and the body structure 101 may be sensed, and thus, positions and/or areas of contact regions of the body structure 101 with the user may be changed according to a body shape of the user. A control unit 205 may determine the body shape of the user based on signals received from one or more sensors of the body structure 101 and may control the body structure 101 based on the body shape. For example, when it is determined that a leg length of the user is greater than that of a current state of the body structure 101, a frame (for example, a frame of the leg massage portion) of the body structure 101, in which a leg of the user is positioned, may be extended.

The massage module 102 may be configured and positioned in the massage device 100 to provide any type of mechanical stimulation to the user accommodated in the body structure 101. As shown in FIG. 1, the massage module 102 may provide mechanical stimulation to various positions while moving along a rail-shaped structure formed inside (or outside) the massage device 100. In such an example, the massage module 102 may have a ball shape or a roller shape.

The massage module 102 may apply pressure to the outside through a pneumatic control method, may apply vibration to the outside using a vibration motor, and may provide stimulation to a massage area by a treatment element or protrusion having any shape being moved through a solenoid method. In addition, since the above-described protrusion or treatment element may be formed of a magnet, iron present in the blood of a human body may be affected by magnetism, thereby further promoting blood circulation.

The massage module 102 may provide a massage function of at least one type of tapping, kneading, chopping, and acupressure according to an operation principle described above.

The audio output unit 103 may provide any type of audio output to the user. The audio output unit 103 outputs a sound and a binaural beat optimized for characteristics of any massage mode provided to the user by the massage device 100, thereby allowing a brain massage corresponding to the massage mode to be performed and allowing a brain to be stimulated. The audio output unit 103 may output sound signals received through a network (not shown) or stored in an internal/external storage medium (not shown). For example, the audio output unit 103 may output a sound under control of a user terminal through a network connection with the user terminal. In addition, the audio output unit 103 may also output any type of sound signal generated in relation to operation of the massage device 100.

In one embodiment, the audio output unit 103 may include a plurality of output units such as a sensor audio output unit disposed at an upper end of a seat unit in contact with the user, a front audio output unit attached to a front end of the armrest at each of left and right sides of the seat unit, and/or a rear audio output unit attached to a rear end of the armrest at each of the left and right sides of the seat unit. In this case, the user may enjoy a stereoscopic sound such as a 5.1-channel sound while receiving a massage from the massage device 100.

Additionally, the audio output unit 103 may also perform a control to transmit an output of a sound signal to an additional headphone or earphone so that the output is directly input to an ear of the user.

The massage device 100 may include the input unit 104 for receiving any selection related to operation control of the massage device from the user. As shown in FIG. 1, the input unit 104 may mean a button and/or a touch screen integrally formed with the massage device 100. As another example, the input unit 104 may include a user terminal or a remote controller which may be positioned remotely from the massage device 100 to communicate with the massage device 100.

The input unit 104 may receive, for example, any selection inputs including selection of a massage mode, selection of a massage type, selection of massage intensity, selection of a massage time, selection of a massage area, selection of a position and operation of the body structure 101, selection of power-on or off of the massage device, selection of an auto mode, selection of operation of a heating function, selection of reproduction of a sound, and the like.

In addition, the input unit 104 may include buttons in the form of a hot key and/or selection buttons for executing direction selection, cancellation, and input according to a preset user setting function, an autonomously preset function, or the like. The input unit 104 may include a touch sensor capable of converting a change in pressure applied to a specific part or a change in capacitance generated in the specific part into an electrical signal. The touch sensor may detect intensity of pressure of a touch as well as a position and area to be touched.

In addition, the input unit 104 may detect an input through a user's speech by utilizing speech recognition technology. In addition, the input unit 104 may be implemented using at least one of a key pad, a dome switch, a (static pressure/capacitive) touch pad, a jog wheel, and a jog switch, but the present disclosure is not limited thereto.

Furthermore, the massage device 100 may include the display 105 for displaying an operating situation of the massage device 100 or a current state of the user. The display 105 according to the embodiments of the present disclosure may include at least one of a liquid crystal display (LCD), a thin film transistor liquid crystal display (TFT LCD), an organic light-emitting diode (OLED), a flexible display, and a three dimensional (3D) display. Some of the displays may be formed as a transparent type or a light transmissive type through which the outside is visible. The some displays may be referred to as transparent displays. A representative example of the transparent display may include a transparent OLED (TOLED) or the like. Two or more displays may be present according to an implementation form of the input unit 104. In addition, the display 105 may be positioned in the input unit 104 or may be present at any position of the massage device 100 by being separated from the input unit 104. The display 105 may display menu screens and graphic objects which are described below. The display 105 may include a touch screen capable of receiving a user input with respect to the graphic object. The display 105 may interact with a user input to switch menus, screen information, graphic objects, and the like.

Although not shown in FIG. 1, the massage device 100 according to one embodiment of the present disclosure may further include a network connection unit for communicating with an external massage device and/or a user terminal through any type of network. The network connection unit may include a wired/wireless connection module for a network connection. For example, wireless local area network (WLAN), Wi-Fi, wireless broadband (WiBro), world interoperability for microwave access (WiMAX), or high speed downlink packet access (HSDPA) may be used as wireless access technology. For example, a digital subscriber line (XDSL), fibers to the home (FTTH), or power line communication (PLC) may be used as wired access technology. In addition, the network connection unit may include a short range communication module to transmit and receive data to and from any device/terminal positioned at a short distance. For example, Bluetooth, radio frequency identification (RFID), infrared data association (IrDA), ultra wideband (UWB), ZigBee, or the like may be used as short range communication technology.

That is, a network in the present disclosure may include WLAN, Wi-Fi, WiBro, WiMAX, HSDPA, IEEE 802.16, long term evolution (LTE), wireless mobile broadband service (WMBS), and the like. Short range communication technology according to the embodiments of the present disclosure may include Bluetooth, RFID, IrDA, UWB, ZigBee, near field communication (NFC), and the like. Wired communication technology according to the embodiments of the present disclosure may include universal serial bus (USB) communication, Ethernet, serial communication, optical/coaxial cable communication, and the like. The above descriptions are merely exemplary descriptions according to the embodiments of the present disclosure, and it is obvious to a person skilled in the art that the scope of the present disclosure is not limited thereto.

Additionally, although not shown in FIG. 1, the massage device 100 according to one embodiment of the present disclosure may include one or more lighting units in the form of a point emission type, a line emission type, and/or a surface emission type. The lighting unit may provide information, which corresponds to an operating situation, any event occurrence, or the like in the massage device 100, as illumination. For example, the lighting unit may include a light-emitting diode (LED) and thus may notify a user of event occurrence through flashing of the LED. Additionally, the lighting unit may change and output a type of light emission, intensity of light emission, and/or a flashing period according to a type of an event.

Figure 2:
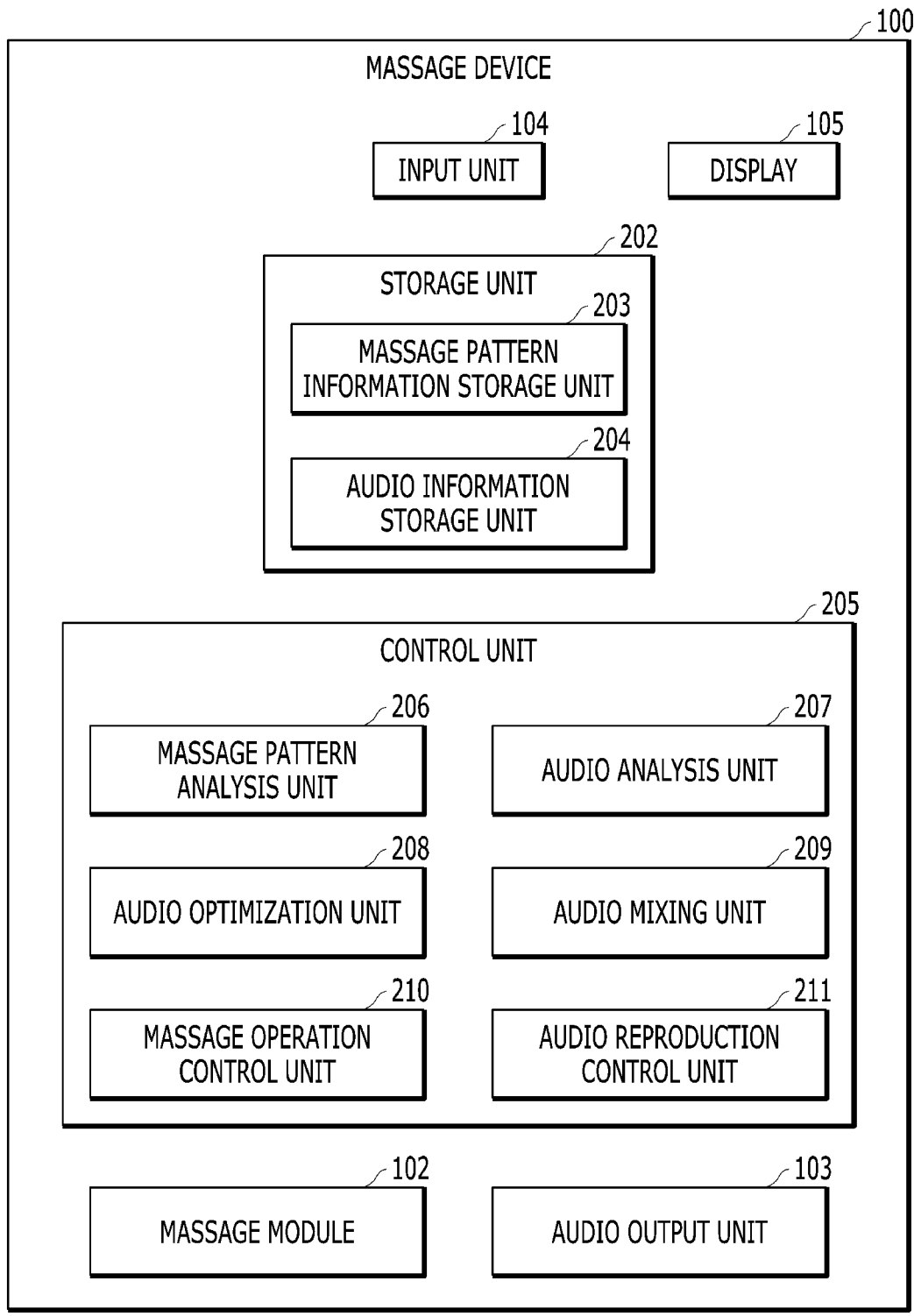
FIG. 2 is an exemplary block diagram illustrating the massage device according to one embodiment of the present disclosure.

FIG. 2 is an exemplary block diagram illustrating the massage device 100 according to one embodiment of the present disclosure.

As shown in FIG. 2, the massage device 100 may include the input unit 104, a storage unit 202, the control unit 205, the massage module 102, and the audio output unit 103. In addition, the storage unit 202 may include a massage pattern information storage unit 203 and an audio information storage unit 204. Furthermore, the control unit 205 may include a massage pattern analysis unit 206, an audio analysis unit 207, an audio optimization unit 208, an audio mixing unit 209, a massage operation control unit 210, and an audio reproduction control unit 211.

The components/modules/units shown in FIG. 2 are merely examples, and according to an implementation type of the massage device 100, the massage device 100 may further include additional components, or some of the above-described components may be omitted.

Since the input unit 104, the massage module 102, and the audio output unit 103 of FIG. 2 have been described with reference to FIG. 1, descriptions thereof will be omitted in the following descriptions given with reference to FIG. 2.

The storage unit 202 may include at least one type of storage medium of a flash memory type memory, a hard disk type memory, a multimedia card micro-type memory, a card-type memory (for example, a secure digital (SD) or extreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The massage device 100 may be operated in relation to a web storage that performs a storage function of the storage unit 202 on the Internet.

The storage unit 202 may temporarily or permanently store any data related to operation of the massage device 100. The storage unit 202 may include the massage pattern information storage unit 203 which stores information about a massage pattern which may be operated by the massage module and the audio information storage unit 294 which stores information about a sound and a binaural beat which may be provided to a user.

The massage pattern information storage unit 203 may store the information about the massage pattern. The information about the massage pattern may include information about a massage provided to the user, which is divided according to various standards. For example, the information about the massage pattern may include at least one of (1) information about a total massage time provided to the user according to a specific mode, (2) information about a massage type indicating a type of mechanical stimulation provided by the massage module, (3) information about a massage area or massage position indicating a position of the massage module, and/or (4) information about massage intensity indicating intensity of mechanical stimulation provided by the massage module.

In addition, the massage pattern information storage unit 203 may pre-store pieces of information about massage patterns according to a specific massage mode (for example, a concentration mode, a meditation mode, a recovery mode, a stretching mode, a sleep mode, a vitality mode, a golf mode, a hip exercise mode, an examinee mode, or a zero gravity mode).

The massage pattern information storage unit 203 may store the pieces of information about the above-described massage patterns through various index values. For example, pieces of information about massage patterns may be stored in a table form of a relational database including columns and rows. In addition, when a massage pattern is changed, the massage pattern information storage unit 203 may store a degree of change in volume of a sound and a degree of change in frequency of a binaural beat between changed patterns. For example, the massage pattern information storage unit 203 may store a scoring value with respect to a volume value of a sound and a scoring value with respect to a frequency of a binaural beat for each massage pattern. As such an example, when a massage area is a "neck," the massage pattern information storage unit 203 may score volume of a sound as 1, and when a massage type is "tapping," the massage pattern information storage unit 203 may score volume of a sound as 0.5. In addition, when a massage area is a "waist," the massage pattern information storage unit 203 may score volume of a sound as 0.5, and when a massage type is "kneading," the massage pattern information storage unit 203 may score volume of a sound as 0.25. In the examples, when a massage pattern is changed from "massage area: neck and massage type: tapping" to "massage area: waist and massage type: kneading," it may be determined how to change volume of a sound using a difference between scoring values. In the above-described examples, a volume value of a sound may be decreased by 0.75, i.e., decreased from a previous value of 1.5 (1+0.5) to a value of 0.75 (0.5+0.25). A volume value of a sound may have a unit of dB but may be a relative value (that is, a decrease by 0.75 may refer to a decrease by 0.75% from a previous value) or may be an absolute value (that is, a decrease by 0.75 may refer to a decrease by 0.75 dB from a previous value). In one embodiment of the present disclosure, a change in frequency of a binaural beat may also be implemented in the same manner as in the above-described examples of the scoring. A degree of change in volume value of a sound and a degree of change in frequency of a binaural beat in the above-described examples may be performed by the audio optimization unit 208 to be described below.

The audio information storage unit 204 may store various types of audio information including a binaural beat, an instrument playing sound, a natural sound, and classical music. In addition, the audio information storage unit 204 may store, for example, audio information in a table form of a relational database including columns and rows.

Furthermore, the audio information storage unit 204 may pre-store audio information according to a specific auto massage mode (for example, a concentration mode, a meditation mode, a recovery mode, a stretching mode, a sleep mode, a vitality mode, a golf mode, or a zero gravity mode).

In addition, the audio information storage unit 204 and the massage pattern information storage unit 203 may interwork with each other, and thus, pieces of information about each other may be mapped in advance and maintained. For example, when a massage area in a massage pattern is a lower half of a body, classical music may be mapped in advance so as to be output. In such an example, a meta table or the like, which stores separate meta information for separately managing mapping information between massage pattern information and audio information, may also be generated.

The massage pattern information storage unit 203 and the audio information storage unit 204 may store massage pattern information and audio information in a user-customized manner. For example, the massage device 100 may receive specific user's preferred massage pattern information and audio information for a predetermined period and periodically update the massage pattern information and the audio information, and thus, even when a user does not separately input his or her own massage pattern or audio information, the massage device 100 may automatically store massage pattern information and audio information, which reflect user preference, (for example, only through a hot key input), so as to provide the massage pattern information and the audio information to the user.

In FIG. 2, the massage pattern information storage unit 203 and the audio information storage unit 204 are illustrated as being distinguished from each other, but the massage pattern information storage unit 203 and the audio information storage unit 204 may be integrated into one storage unit according to embodiments.

The control unit 205 may control overall operations of the massage device 100 and operations of components in the massage device 100. For example, the control unit 205 may analyze information about a massage pattern and change volume of a sound and a frequency of a binaural beat over time on the basis of massage pattern analysis information. In addition, the control unit 205 may generate audio information to be provided to the user by mixing the binaural beat and the sound changed over time. Furthermore, the control unit 205 may control operation of the massage module 102 and operation of the audio output unit 103.

The embodiments described in the present disclosure, in particular, the embodiments described in relation to the control unit 205, may be implemented, for example, by one or more processors in a computer-readable storage medium or any storage medium similar thereto by using software, hardware, or a combination thereof.

According to a hardware implementation, the embodiments described herein may be implemented using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and electrical units for executing other functions. In some cases, the embodiments described in the present specification may be implemented by only the control unit 205.

According to a software implementation, the embodiments such as procedures or functions described in the present specification may be implemented using separate software modules. Each of the software modules may perform one or more functions and operations described in the present specification. A software code may be implemented with a software application made using an appropriate program language. The software code may be stored in the storage unit 202 and may be executed by the control unit 205.

The massage pattern analysis unit 206 may generate massage pattern analysis information by analyzing information about a massage pattern stored in the massage pattern information storage unit 203.

For example, the massage pattern analysis information may include massage step identification information for identifying each of a plurality of massage steps determined based on a massage mode received from a user. The massage step identification information may include time data about a massage step. For example, when a total massage time of a specific massage mode is 20 minutes and a massage step is identified as four steps, five minutes may be allocated to a massage time for each step. Therefore, through the massage step identification information, when a current massage time is twelve minutes, it may be identified that a second massage step is being performed. In such an example, when a massage mode input from a user is a concentration mode, a first step of the plurality of massage steps may include a step of changing a state of the user from an arousal state to a stable state, and a last step of the plurality of massage steps may include a step of changing the state of the user from the stable state to the arousal state. When a massage mode input from a user is a meditation mode, a first step of the plurality of massage steps may include a step of transitioning a state of the user from an arousal state to a stable state, and the remaining steps of the plurality of massage steps may include steps of inducing the user to increasingly deeper stable states as a step is changed to a next step.

As another example, the massage pattern analysis information may include massage type identification information for indentifying a plurality of massage types including at least one of tapping, kneading, and acupressure, which are determined based on a massage mode received from a user or determined by a massage type selection input received from the user. Time data indicating time information for each massage type may be allocated to the massage type identification information. For example, in a sleep mode, a massage type in the form of "tapping" may initially last for zero minutes to five minutes.

As still another example, the massage pattern analysis information may include massage position identification information for indentifying a body position of a user (for example, a neck, a shoulder, a back, a waist, a hip, a leg, and/or a foot), to which a massage function is provided by the massage device. The massage position identification information may be determined based on a massage mode received from a user or may be determined by a massage position selection input received from the user. The massage position identification information may include time data about a massage position and may have time information allocated for each massage position in advance.

As yet another example, the massage pattern analysis information may include massage intensity identification information for indentifying massage intensity provided to a user by the massage module (for example, information for dividing a level of a massage into upper, medium, and lower levels or strong, medium, and weak levels, or information for dividing massage intensity with numerals). The massage intensity identification information may be determined based on a massage mode received from a user or may be determined by a massage intensity selection input received from the user. Since the massage intensity identification information includes time data about massage intensity, a time value of a massage that lasts for each massage intensity may be analyzed.

In addition, the massage pattern analysis unit 206 may divide a massage mode to be provided to a user into a plurality of massage steps based on a massage mode received from the user and may determine time data about each of the divided massage steps, thereby generating the massage pattern analysis information. The massage pattern analysis information includes time data about each of various types of massage patterns so that points at which a massage pattern is changed may be distinguished through, for example, a time stamp.

The audio analysis unit 207 may generate audio analysis information by analyzing audio information stored in the audio information storage unit 204. The audio analysis unit 207 may generate sound analysis information by analyzing a sound which may be provided to a user. For example, based on a sound pitch, a sound flow, and/or a total reproduction time of a specific sound, the audio analysis unit 207 may divide the specific sound into a plurality of steps (for example, introduction, development, turn, and conclusion steps). That is, the audio analysis unit 207 may divide a sound provided to a user into the plurality of steps and may determine time data about each of the divided sound steps, thereby generating sound analysis information. The sound analysis information may include inflection points changed over time with respect to the specific sound.

The audio optimization unit 208 may change volume of a sound and a frequency of a binaural beat over time on the basis of the massage pattern analysis information analyzed from the massage pattern analysis unit 206.

For example, the audio optimization unit 208 may determine a time point at which a previous massage step is changed to a next massage step in a plurality of massage steps based on time data in massage step identification information and may determine to change volume of a sound to be reproduced and/or a frequency of a binaural beat at a change time point.

The audio optimization unit 208 may determine a time point at which a massage type is changed in a plurality of massage types implemented by the massage module based on time data in massage type identification information and may determine to change volume of a sound and/or a frequency of a binaural beat at a change time point.

The audio optimization unit 208 may determine a time point at which a massage position is changed in a plurality of massage positions implemented by the massage module based on time data in massage position identification information and may determine to change volume of a sound and/or a frequency of a binaural beat at a change time point. The audio optimization unit may additionally change the volume of the sound so as to be increased as a massage position in the massage position identification information that is closer to a face of a user. Therefore, when a position of the massage module is close to an ear of the user, audio information to be output to the user may be prevented from being cancelled by noise caused by operation of the massage module, and thus, optimal audio information without noise may be provided to the user.

The audio optimization unit 208 may determine a time point at which massage intensity is changed in a plurality of massage intensities implemented by the massage module based on time data in massage intensity identification information and may change volume of a sound and/or a frequency of a binaural beat at a change time point. The audio optimization unit 208 may additionally change the volume of the sound so as to be increased as the massage intensity is increased in the massage intensity identification information. Therefore, when the massage intensity performed by the massage module is increased, audio information to be output to the user may be prevented from being canceled by noise caused by operation of the massage module, and thus, optimal audio information without noise may be provided to the user.

The audio optimization unit 208 may change volume of a sound and a frequency of a binaural beat over a time on the basis of the massage pattern analysis information analyzed from the massage pattern analysis unit 206 and the sound analysis information analyzed from the audio analysis unit 207.

The audio optimization unit 208 may compare time data included in the massage pattern analysis information analyzed from the massage pattern analysis unit 206 with time data included in the sound analysis information analyzed from the audio analysis unit 207, may determine change time points at which at least one of massage steps and sound steps is changed, and may determine to change volume of a sound and/or a frequency of a binaural beat at the determined change time points.

The audio optimization unit 208 may determine various change points based on a massage time, a massage type, a massage area, massage intensity, and a sound pitch, a sound flow, and/or a total reproduction time of a sound and may change volume of a sound and/or a frequency of a binaural beat at the change points, thereby allowing a sound optimized for a massage pattern and a music pattern to be provided to a user and allowing a brain massage to be performed.

The audio optimization unit 208 may determine a first change causative factor between sound time steps at each time point to which a first time stamp included in audio analysis information analyzed from the audio analysis unit 207 is allocated and may determine a second change causative factor between massage steps at each time point at which a second time stamp included in massage pattern analysis information analyzed from the massage pattern analysis unit 206 is allocated. That is, the massage pattern analysis information may include a plurality of factors such as a massage type, a massage area, massage intensity, a step for each massage flow, and the audio analysis information may also include a plurality of factors such as a sound pitch, a sound flow, a reproduction time of a sound, and the like with respect to a sound. Accordingly, each of the first time stamp and the second time stamp may include all of change points between the factors. Therefore, how much to change volume of a sound and/or a frequency of a binaural beat at time stamp points should be determined only with change factors at the change points.

For example, when only a massage area is changed at a point of the second time stamp, amounts of changes in volume of a sound and/or in frequency of a binaural beat may be determined by comparing only a value of a massage area in a previous pattern with only a value of a massage area in a next massage pattern. That is, the audio optimization unit 208 may determine change intensity before and after a change based on the determined first change causative factor and may determine change intensity before and after a change on the basis of the determined second change causative factor, thereby determining amounts of changes in volume of the sound and/or in frequency of the binaural beat at a time point to which the first time stamp is allocated and at a time point to which the second time stamp is allocated. Here, the first change causative factor may include a factor selected from information about a sound pitch, information about a sound flow, and information about a reproduction time of a sound, and the second change causative factor may include a factor selected from information of a massage flow, information about a massage type, information about a massage area, and information about massage intensity.

In exemplary embodiments according to functions of the control unit 205, the audio analysis unit 207 may analyze a sound which may be provided to a user, thereby dividing the sound into a plurality of time steps based on a progress flow of the sound. In addition, the audio analysis unit 207 may allocate the first time stamp to each of points at which the plurality of divided time steps are distinguished, thereby generating sound analysis information. The massage pattern analysis unit 206 may determine a plurality of massage steps indicating states of a user induced by a massage according to a massage mode received from the user. In addition, the massage pattern analysis unit 206 may allocate the second time stamp to each of points at which the plurality of determined massage steps are distinguished, thereby generating massage pattern analysis information. Furthermore, the audio optimization unit 208 may determine to change volume of a sound to be reproduced and/or a frequency of a binaural beat at a time point to which the first time stamp is allocated and at a time point to which the second time stamp is allocated (that is, at any points to which the first time stamp and the second time stamp are allocated).

The audio mixing unit 209 may mix a binaural beat and a sound changed by the audio optimization unit 208 over time, thereby generating audio information to be provided to a user. A mixing operation and an audio information generating operation of the audio mixing unit 209 may optionally be replaced by the audio optimization unit 208.

The massage operation control unit 210 may control operation of the massage module 102. For example, the massage operation control unit 201 may transmit a signal to the massage module 102 to control an operation position, operation intensity, an operation type, and/or an operation time of the massage module 102. Accordingly, the massage module 102 may provide a massage function to a user under control of the massage operation control unit 210.

The audio reproduction control unit 211 may control operation of the audio output unit 103. For example, the audio reproduction control unit 211 may transmit a signal to the audio output unit 103 to control a type, intensity, and/or a duration time of a sound output from the audio output unit 103. Accordingly, the audio output unit 103 may output audio information to a user under control of the audio reproduction control unit 211.

Figure 3:
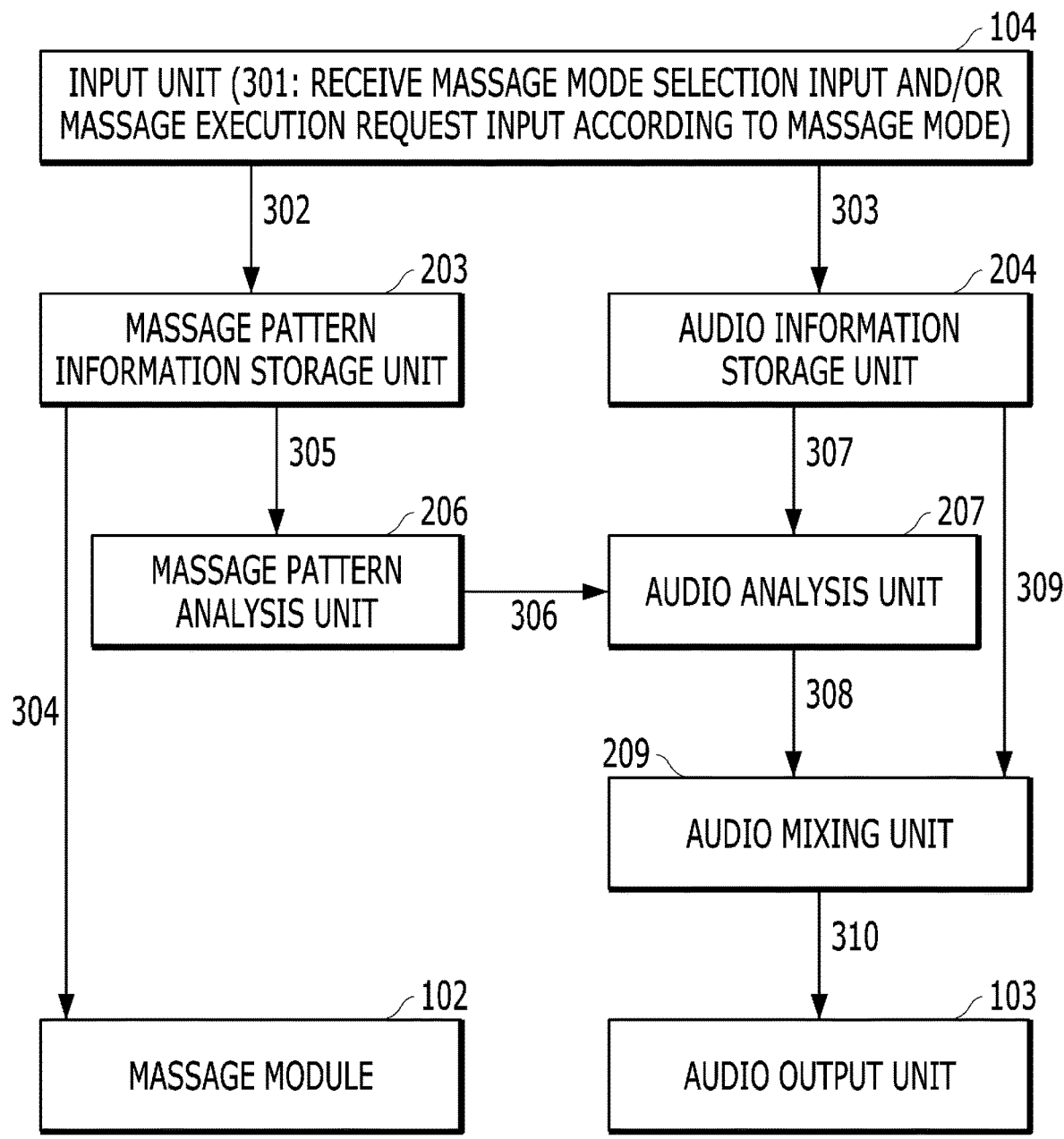
FIG. 3 is a flowchart of exemplary operations implemented by the massage device according to one embodiment of the present disclosure.

FIG. 3 is a flowchart of exemplary operations implemented by the massage device 100 according to one embodiment of the present disclosure.

The operations shown in FIG. 3 are merely examples, and some of the operations of FIG. 3 may be omitted or additional operations may be added according to embodiments.

According to one embodiment, the massage device 100 may receive a massage mode selection input and/or a massage execution request input according to a massage mode from a user through the input unit 104 (301). The input from the user may be directly performed through input buttons integrated into the massage device 100 or predetermined hot key buttons or may be wirelessly performed through an external terminal (or a remote controller) or the like. When the user selects an auto massage mode, operations of analyzing and processing data stored in the massage pattern storage unit 203 and the audio information storage unit 204 may be executed (302 and 303).

Data for a massage pattern analysis in the massage pattern information storage unit 203 may be read by the massage pattern analysis unit 206 (305). That is, the massage pattern analysis unit 206 may access the data stored in the massage pattern information storage unit 203 to generate massage pattern analysis information.

In addition, the massage pattern information storage unit 203 may also control a mechanical stimulation generating operation of the massage module 102 by directly transmitting a specific mode stored in the massage pattern information storage unit 203 or massage pattern information according to user selection to the massage module 102 (304). Step 304 may also be performed by the massage operation control unit 210.

The massage pattern analysis unit 206 may transmit the massage pattern analysis information to the audio analysis unit 207 (306). In another embodiment, the massage pattern analysis unit 206 may transmit the massage pattern analysis information to the audio optimization unit. The massage pattern analysis unit 206 may analyze characteristics of a massage pattern, such as a total massage time, a massage step, a massage type, a massage area, and massage intensity and may select index values of the characteristics to transmit the index values to the audio analysis unit 207 or the audio optimization unit.

The audio information storage unit 204 may transmit stored audio information such as a binaural beat, an instrument playing sound, and a natural sound to the audio analysis unit 207 (307). In addition, the audio information storage unit 204 may transmit the stored audio information such as the binaural beat, the instrument playing sound, and the natural sound to the audio mixing unit 209 (309).

The audio analysis unit 207 may generate audio analysis information to transmit the audio analysis information to the audio mixing unit 209 (308). In one embodiment, the audio analysis information may include information in which audio information is divided into a plurality of steps or may also include a type of audio information in which volume of a sound and/or a frequency of a binaural beat are changed over time. Some of operations of the audio analysis unit 207 (for example, an operation of changing volume of a sound and/or a frequency of a binaural beat over time) may also be implemented by the audio optimization unit.

The audio mixing unit 209 may generate one type of music information by mixing music and a binaural beat based on optimized elements transmitted from the audio analysis unit 207 or the audio optimization unit. The audio information may be transmitted to the audio output unit 103 (310), and thus, the audio output unit 103 may be controlled so that a user on which a massage function is being performed may listen to music with the optimized elements. Furthermore, the control of the audio output unit 103 may also be implemented by the audio reproduction control unit 211.

The massage module 102 may provide massage operations (that is, mechanical stimulation) to a user under control of the massage pattern information storage unit 203 and/or the massage operation control unit 210.

Figure 4:
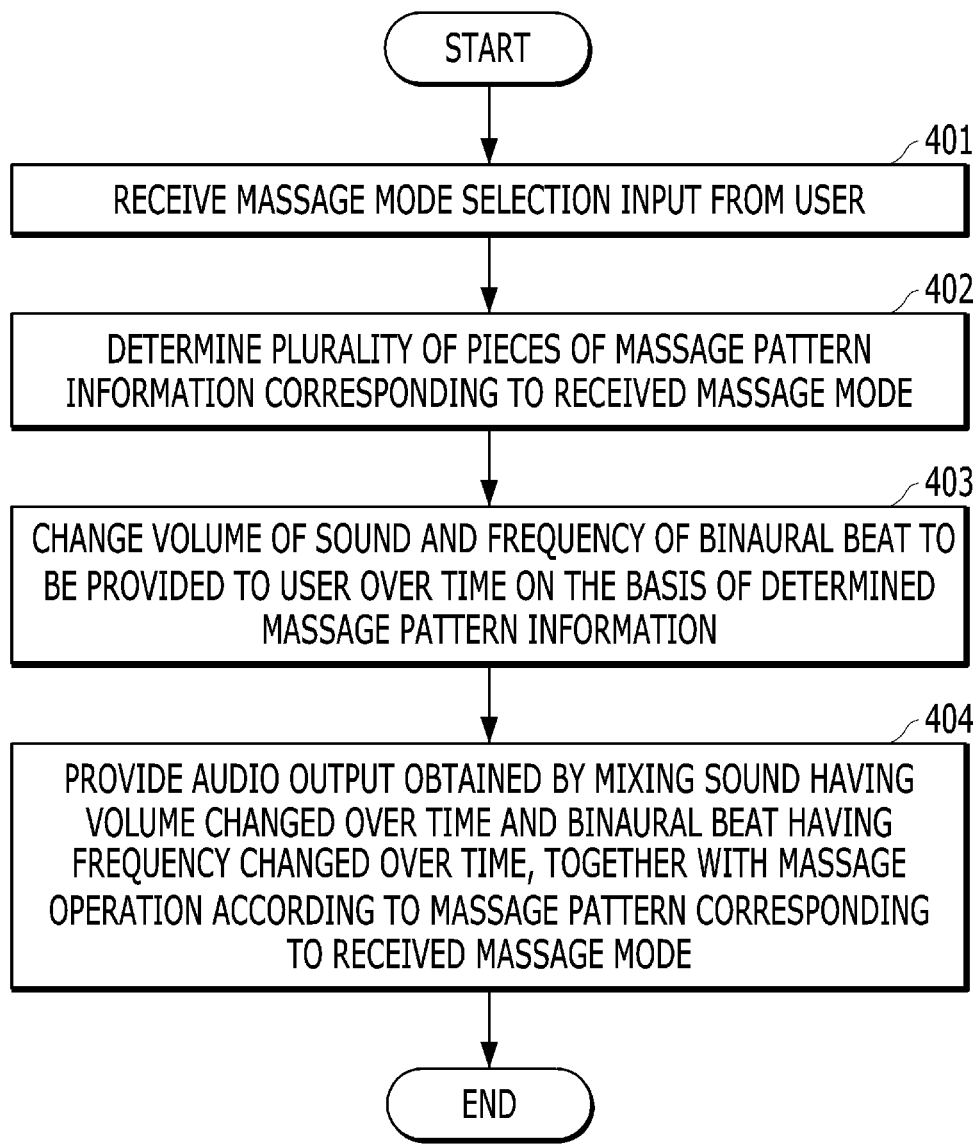
FIG. 4 is a flowchart of an exemplary method of providing a massage function performed by the massage device according to one embodiment of the present disclosure.

In embodiments according to examples shown in FIG. 4, a total massage time of a massage mode may be determined, for example, as 20 minutes or 30 minutes. When the total massage time is 20 minutes (for example, in a concentration mode), 5 minutes may be allocated to each massage step, and thus, four massage steps may be present. When the total massage time is 30 minutes (for example, in a meditation mode), 5 minutes may be allocated to each of a first massage step and a third massage step, and 10 minutes may be allocated to each of a second massage step and a fourth massage step. Therefore, since massage steps for each massage mode are divided over a time, points, at which volume of a sound and/or a frequency of a binaural beat are changed over time, may be distinguished. In such an example, when volume of a sound in the first massage step is ten, volume of a sound in the second massage step may be increased by one to two, volume of a sound in the third step may be maintained to be equal to that in the second massage step, and volume of a sound in the fourth massage step may be decreased by one to two as compared with the second massage step. In addition, when a frequency of a binaural beat in the first massage step is in a range of 10 Hz to 20 Hz, a frequency of a binaural beat may be changed to be in a range of 5 Hz to 10 Hz in the second step, be in a range of 3 Hz to 7 Hz in the third step, and be in a range of 2 Hz to 5 Hz in the fourth step. Here, volume of a sound may have a unit of dB but may be a relative value (that is, a decrease by one to two from a current size may be interpreted as being decreased by 1% to 2%) or may be an absolute value (that is, a decrease by one to two from a current size may be interpreted as being decreased by 1 dB to 2 dB).

In addition, in an example of a massage type, when the massage type is tapping, the massage device 100 may increase volume of a sound by 0.1 to 0.5 as compared with other massage types. When the massage type is acupressure, the massage device 100 may decrease a frequency of a binaural beat by 0.1 Hz to 1 Hz as compared with other massage types.

In addition, in an example of a massage area, when the massage area is a neck, the massage device 100 may increase volume of a sound by 0.1 to 0.5 as compared with when the massage area is a lower half of a body. In addition, the massage device 100 may decrease a frequency of a binaural beat by 0.1 Hz to 1 Hz as compared with when the massage area is the lower half of the body.

Furthermore, in an example of massage intensity, when the massage intensity is "strong," the massage device 100 may increase volume of a sound by 0.1 to 0.5 as compared with when the massage intensity is "medium." When the massage intensity is "weak," the massage device 100 may decrease a frequency of a binaural beat by 0.1 Hz to 1 Hz as compared with when the massage intensity is "medium."

As described above, the massage device 100 according to one embodiment of the present disclosure may determine inflection points for changing a frequency of a binaural beat and/or volume of a sound in real time by using time values with respect to various types of massage patterns. As a result, since a user may receive an optimal sound and binaural beat according to a massage-receiving pattern, an increased massage effect may be provided to the user. Furthermore, in a case in which a massage is provided by changing volume of a sound and a frequency of a binaural beat in real time according to one embodiment of the present disclosure, as compared with a case in which a massage is received through a general conventional massage device, when a massage is received for the same time in relation to a relaxation mode, occurrence of a beta wave, which is a brain wave related to agility, arousal, concentration, and cognitive power, may be significantly reduced.

FIGS. 4 to 8 are flowcharts of exemplary methods of providing a massage function performed by the massage device 100 according to the embodiments of the present disclosure. Although the methods for providing the massage function described with reference to FIGS. 4 to 8 may be implemented as separate embodiments, it is also obvious to a person skilled in the art that embodiments by any combination of the separate embodiments are also included in the scope of the present disclosure. In addition, although the embodiments of FIGS. 4 to 8 are described as a method that includes the forms of "steps," it is also obvious to a person skilled in the art that the steps may be changed to the form of "means" functionally representing a corresponding operation as well as the forms of "operations," "modules," "logics," and/or "commands by which a processor performs a program stored on a computer-readable storage medium.

FIG. 4 is a flowchart of an exemplary method of providing a massage function performed by the massage device according to one embodiment of the present disclosure.

Steps shown in FIG. 4 are merely examples, and additional steps may be present or some of the steps may be omitted. In addition, among the descriptions of the steps described with reference to FIG. 4, those to be described with reference to FIGS. 1 to 3 will be referenced for those previously described with reference to FIGS. 1 to 3, and for the sake of clarity, corresponding descriptions will be omitted herein.

As shown in FIG. 4, the massage device 100 may receive a massage mode selection input from a user (401).

In response to the massage mode selection input, the massage device 100 may determine massage pattern information corresponding to a received massage mode (402). That is, the massage device 100 may retrieve information about a massage pattern pre-stored for each massage mode received from a user (for example, a total massage time, a massage progress step, a massage type, massage intensity, or a massage area). As described above, the information about the massage pattern may refer to a massage pattern value to which a time value is allocated. The massage device 100 may change a frequency of a binaural beat and/or volume of a sound at the time value at which a massage pattern is changed (403).

For example, when, in information about a massage pattern, a current massage step according to a total massage time is a "first step," a massage region is a "hip," a massage type is "acupressure," and massage intensity is "medium," values for changing volume of a sound and a frequency may be scored and stored in a unit of each piece of massage pattern information. Then, when a massage pattern is changed, for example, when a massage step is changed to a "second step," information about a massage pattern identical to the massage step (i.e., a massage step of the first step) may be found, and a scoring value allocated to the first step may be compared with a scoring value allocated to the second step, and thus, volume of a sound and a frequency of a binaural beat may be changed by a difference between the scoring values. After that, at a time point at which information about another type of massage pattern is generated (for example, a massage area is changed from a "hip" to a "neck"), scoring values allocated to pieces of information about corresponding massage patterns may be compared with each other, and thus, it may be determined how much to change volume of a sound and a frequency of a binaural beat.

Then, the massage device 100 may provide an audio output obtained by mixing a sound having volume changed over time and a binaural beat having a frequency changed according to a frequency, together with a massage operation according to a massage pattern corresponding to the received massage mode.

Figure 5:
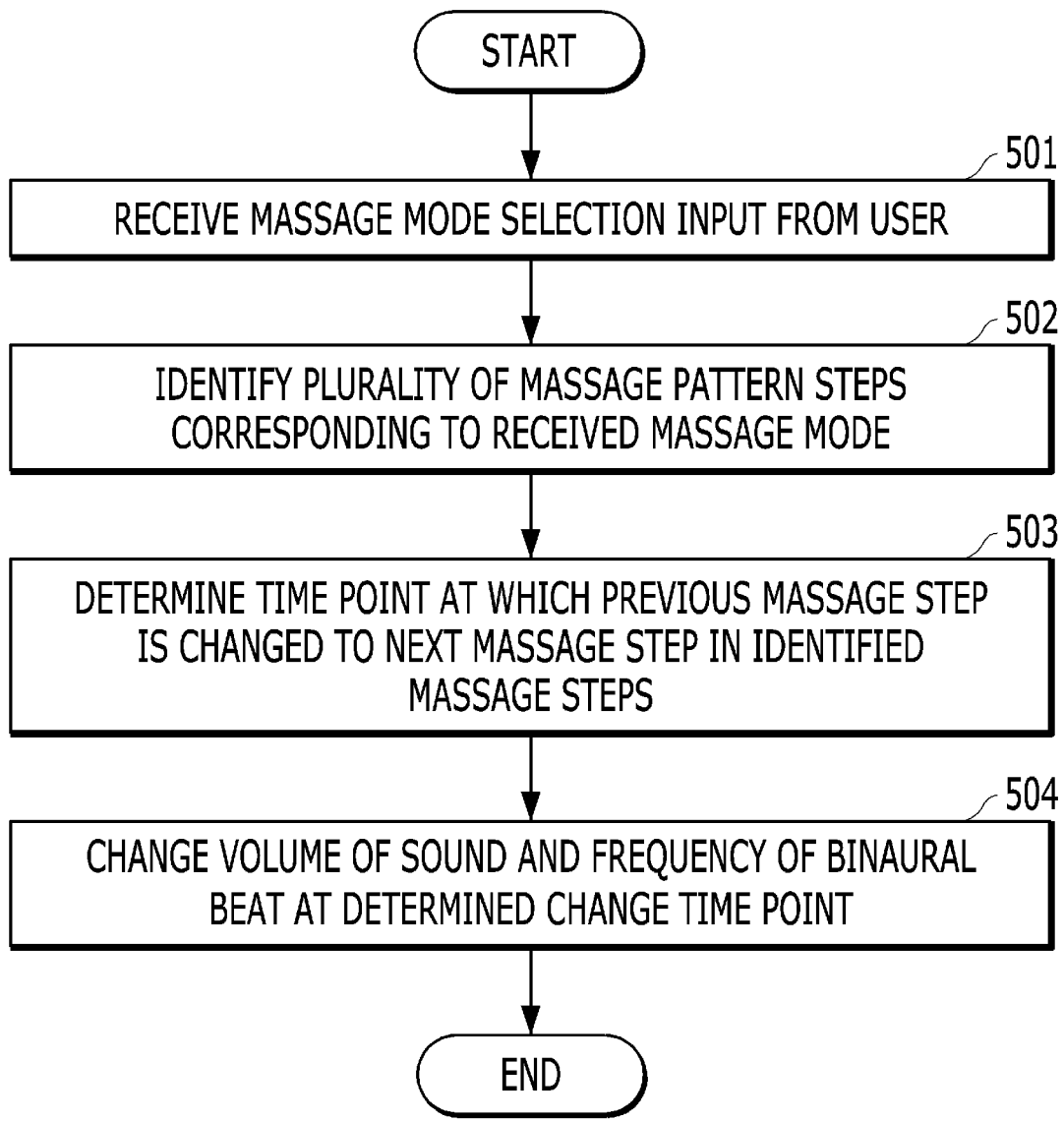
FIG. 5 is a flowchart of an exemplary method of providing a massage function performed by the massage device according to one embodiment of the present disclosure.

FIG. 5 is a flowchart of an exemplary method of providing a massage function performed by the massage device according to one embodiment of the present disclosure.

The massage device 100 may receive a massage mode selection input from a user (501). In response to the massage mode selection input, the massage device 100 may identify a plurality of massage steps corresponding to a received massage mode (502). Here, the plurality of massage steps may refer to, for example, steps obtained by dividing a total massage time for each massage flow (for example, massage flow steps: steps obtained by dividing massage flows related to a change in state of a user).

When the identification of the massage steps is completed, the massage device 100 may determine a time point at which a previous massage step is changed to a next massage step in the identified massage steps (503). That is, the massage device 100 may determine a change time point between the massage steps.

Then, the massage device 100 may change volume of a sound and/or a frequency of a binaural beat at a determined change time point (504). Here, the massage device 100 may determine what a change causative factor is at the determined change time point. For example, when it is determined that a second step is changed to a third step in steps divided by flows according to a concentration mode, a scoring value allocated to the second step may be compared with a scoring value allocated to the third step. Thus, based on a difference value between the scoring values, the massage device 100 may determine amounts of changes in volume of a sound and/or in a frequency of a binaural beat.

Figure 6:
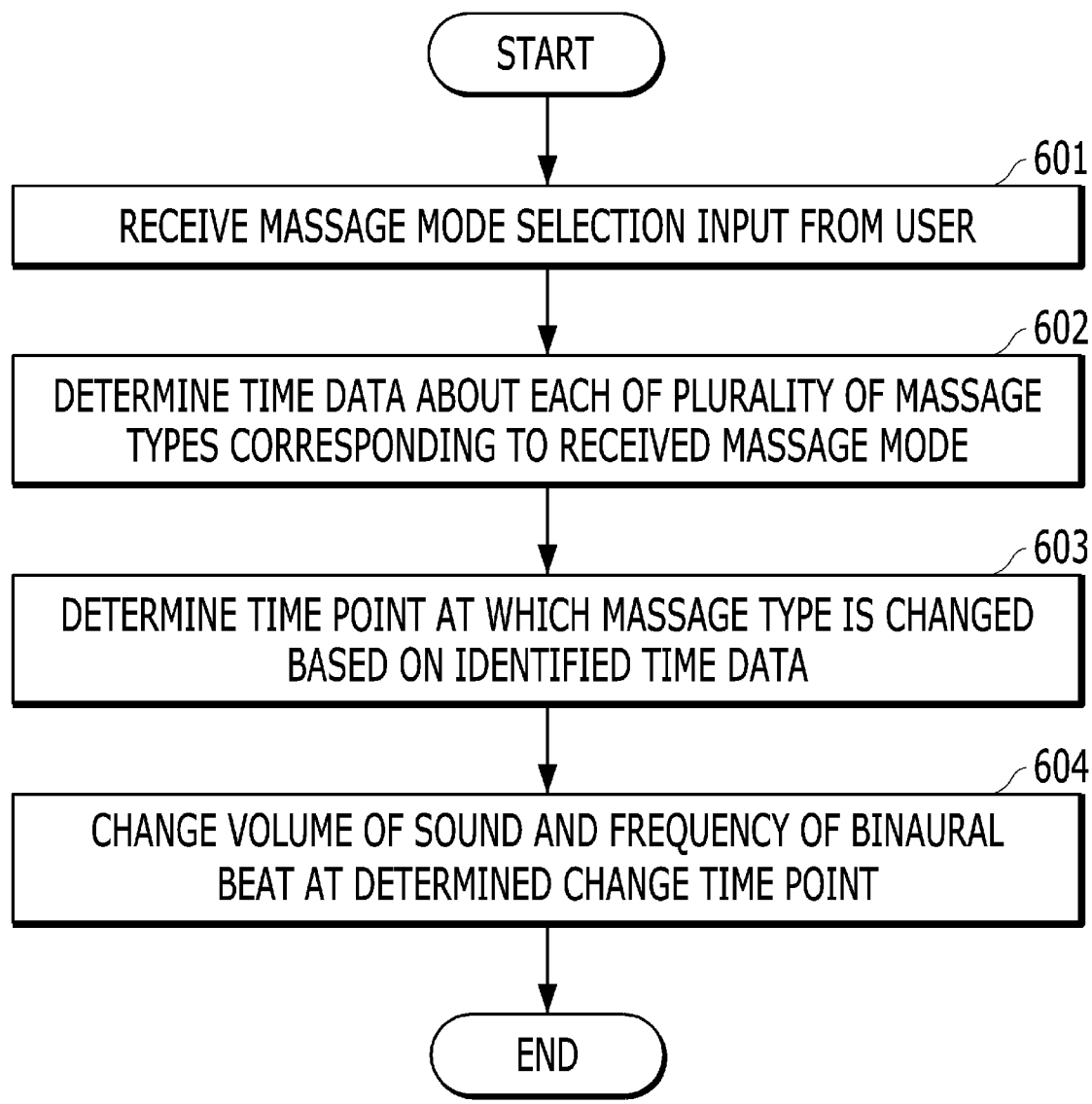
FIG. 6 is a flowchart of an exemplary method of providing a massage function performed by the massage device according to one embodiment of the present disclosure.

FIG. 6 is a flowchart of an exemplary method of providing a massage function performed by the massage device according to one embodiment of the present disclosure.

The massage device 100 may receive a massage mode selection input from a user (601). In response to the massage mode selection input, the massage device 100 may identify a plurality of massage steps corresponding to a received massage mode (602). Here, the plurality of massage steps may refer to, for example, steps divided by factors related to massage types such as tapping, acupressure, and kneading.

When the identification of the massage types is completed, the massage device 100 may determine a time point at which a previous massage step is changed to a next massage step in the identified massage types (603). That is, the massage device 100 may determine a change time point between the massage types.

Then, the massage device 100 may change volume of a sound and/or a frequency of a binaural beat at the determined change time point (604). Here, the massage device 100 may determine a change causative factor at the determined change time point. For example, when the change time point is a time point at which a massage type of "kneading" is changed to a massage type of "tapping," a scoring value allocated to the "kneading" may be compared with a scoring value allocated to the "tapping." Thus, based on a difference value between the scoring values, the massage device 100 may determine amounts of changes in volume of a sound and/or in a frequency of a binaural beat.

Figure 7:
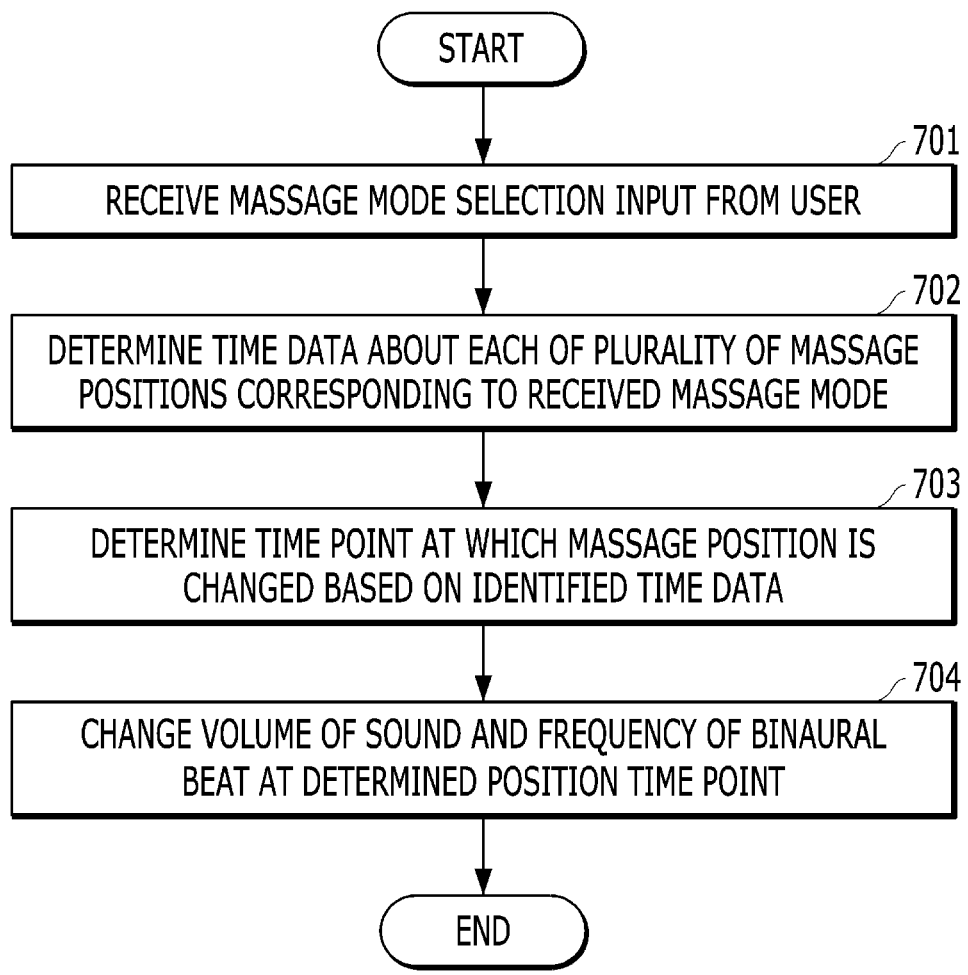
FIG. 7 is a flowchart of an exemplary method of providing a massage function performed by the massage device according to one embodiment of the present disclosure.

FIG. 7 is a flowchart of an exemplary method of providing a massage function performed by the massage device according to one embodiment of the present disclosure.

The massage device 100 may receive a massage mode selection input from a user (701). In response to the massage mode selection input, the massage device 100 may identify a plurality of massage positions corresponding to a received massage mode and may determine time data about each of the identified massage positions (702). Here, the plurality of massage positions may refer to, for example, steps divided by factors related to massage areas such as a neck, a hip, a waist, and a leg.

When the identification of the massage positions or massage areas is completed, the massage device 100 may determine a time point at which a previous massage position is changed to a next massage position based on a time value in the identified massage positions or massage areas (703). That is, the massage device 100 may determine a change time point between the massage positions.

Then, the massage device 100 may change volume of a sound and/or a frequency of a binaural beat at the determined change time point (704). Here, the massage device 100 may determine a change causative factor at the determined change time point. For example, when the change time point is a time point at which a massage position with respect to a "neck" is changed to a massage position with respect to a "leg," a scoring value allocated to the "neck" may be compared with a scoring value allocated to the "leg." Thus, based on a difference value between the scoring values, the massage device 100 may determine amounts of changes in volume of a sound and/or in a frequency of a binaural beat.

Figure 8:
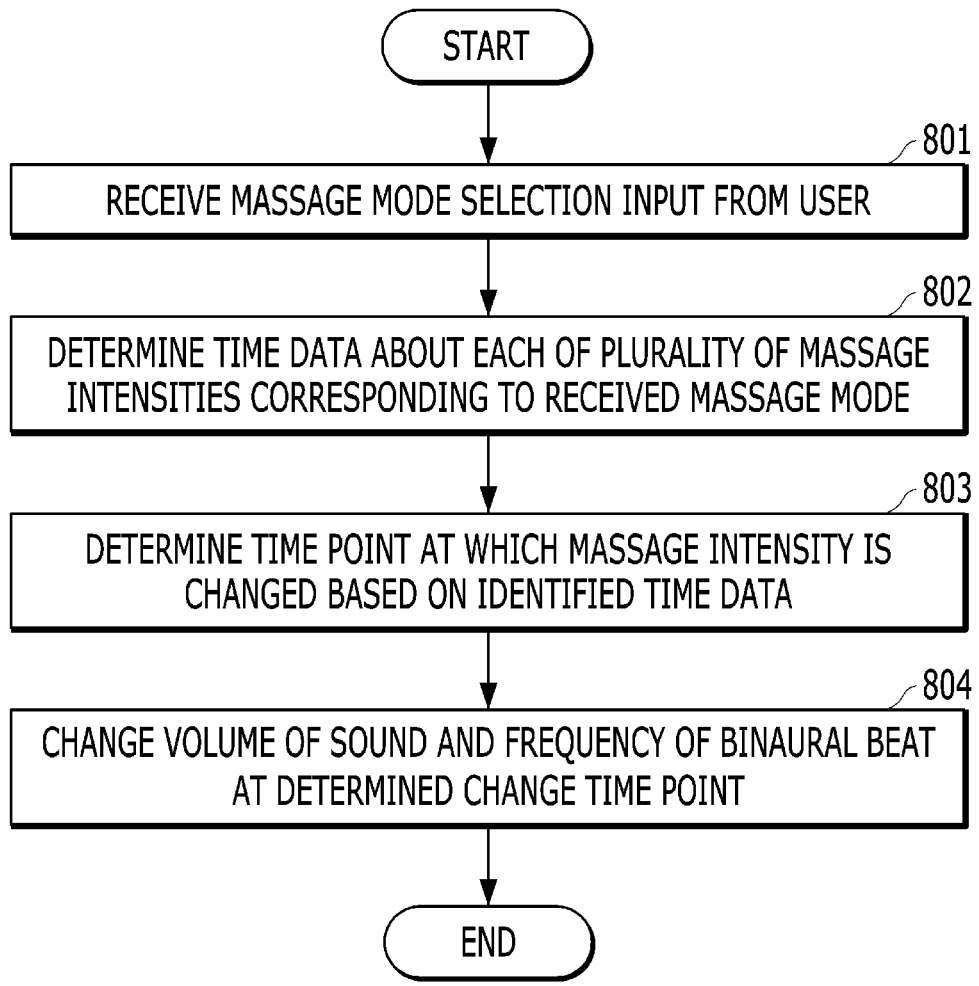
FIG. 8 is a flowchart of an exemplary method of providing a massage function performed by the massage device according to one embodiment of the present disclosure.

FIG. 8 is a flowchart of an exemplary method of providing a massage function performed by the massage device according to one embodiment of the present disclosure.

The massage device 100 may receive a massage mode selection input and/or a massage intensity selection input from a user (801). In response to the massage mode selection input and/or the massage intensity selection input, the massage device 100 may identify a plurality of massage intensities corresponding to a received massage mode and may determine time data about each of the identified massage intensities (802). Here, the plurality of massage intensities may be, for example, indexes indicating massage intensities and may refer to steps divided by factors related to levels such as strong, medium, and weak levels. Steps with respect to the massage intensities may include time data allocated to each of the steps. The time value may refer to a time value during which a massage lasts for each massage intensity (strength).

When the identification of the massage intensities is completed, the massage device 100 may determine a time point at which massage intensity is changed from a previous massage intensity to a next massage intensity on the basis of a time value in the identified massage intensities (803). That is, the massage device 100 may determine a change time point between the massage intensities.

Then, the massage device 100 may change volume of a sound and/or a frequency of a binaural beat at the determined change time point (804). Here, the massage device 100 may determine a change causative factor at the determined change time point. For example, when the change time point is a time point at which a massage intensity step with respect to "strong" is changed to a massage intensity step with respect to "weak," a scoring value allocated to the term "strong" may be compared with a scoring value allocated to the term "weak." Thus, based on a difference value between the scoring values, the massage device 100 may determine amounts of changes in volume of a sound and/or in a frequency of a binaural beat.

Figure 9:
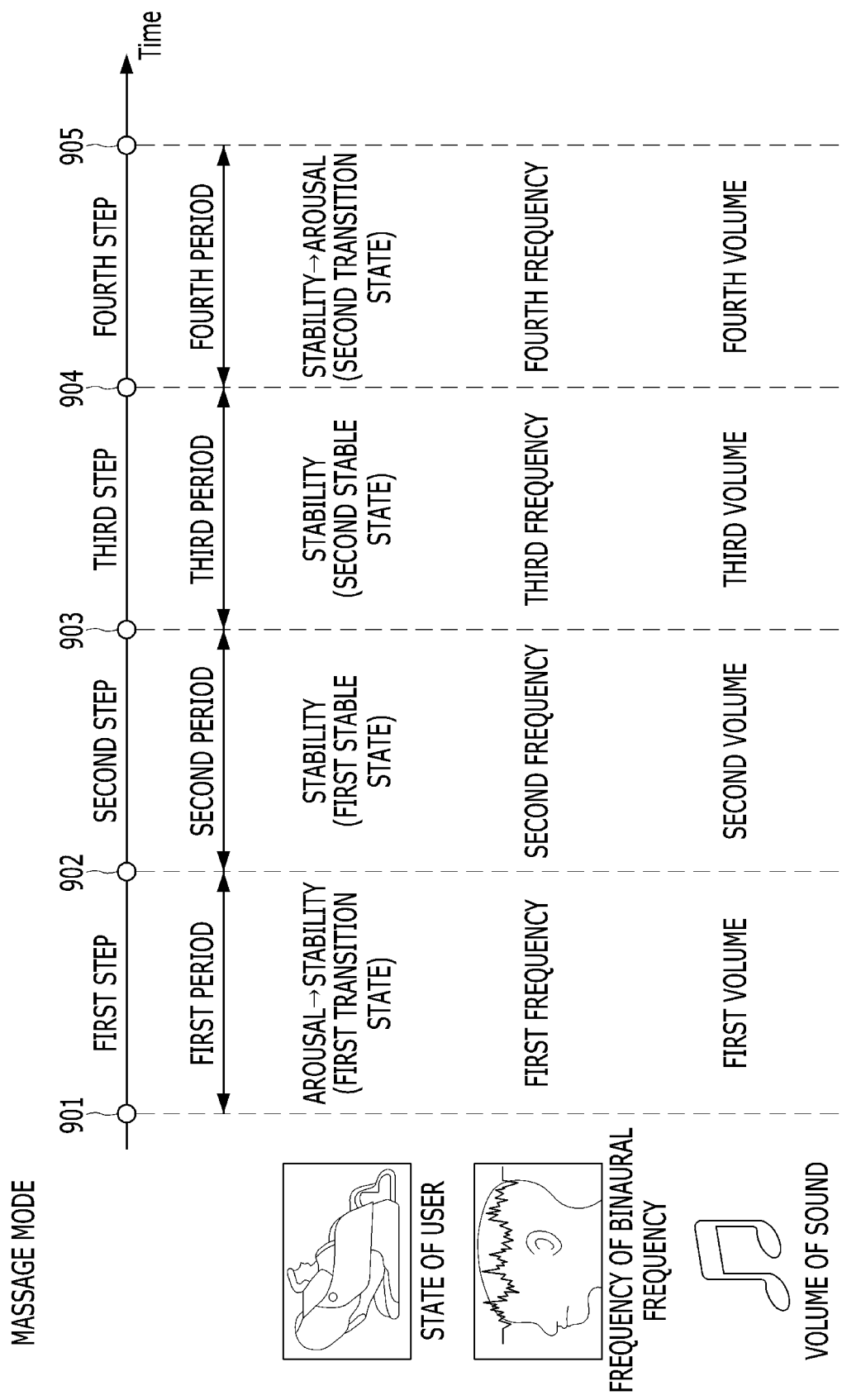
FIG. 9 illustrates an exemplary method of changing a frequency of a binaural beat and volume of a sound according to a specific massage mode according to one embodiment of the present disclosure.

FIG. 9 illustrates an exemplary method of changing a frequency of a binaural beat and volume of a sound according to a specific massage mode according to one embodiment of the present disclosure.

In one embodiment of the present disclosure, massage pattern information and audio information according to an auto massage mode (for example, a concentration mode, a meditation mode, a recovery mode, a stretching mode, a sleep mode, a vitality mode, a golf mode, or a zero gravity mode) may be pre-stored.

For example, a sleep mode refers to a massage mode which induces a user to gradually enter a sleep state while a massage type is changed from a massage concentrated on tapping with respect to a massage area of a back to a massage concentrated on kneading and acupressure. According to the embodiments of the present disclosure, when volume of a sound and/or a frequency of a binaural beat are changed over time on the basis of massage pattern information and/or audio information, it has been found that sleep latency, which is a time taken for a subject to fall asleep, is decreased by 30% (average seven minutes) as compared with a conventional massage device, and an index, which is an N3 sleep time indicating a sleep depth, is increased by 100% or more (average thirteen minutes), and a sensory sleep time is also increased by 10% (average forty minutes).

For example, a relaxation mode may refer to a full body massage mode which performs a massage concentrated on acupressure in the order of a shoulder massage, a back massage, and a waist massage (that is, there is uniqueness to a massage area and a massage type). In a case in which a massage is provided by changing volume of a sound and a frequency of a binaural beat in real time according to one embodiment of the present disclosure, as compared with a case in which a massage is received through a general conventional massage device, when a massage is received for the same time in relation to a relaxation mode, occurrence of a beta wave, which is a brain wave related to agility, arousal, concentration, and cognitive power, may be significantly reduced.

For example, an examinee mode or a concentration mode may refer to a waist massage-concentrated mode which is a massage for an examinee sitting for a long time and of which a massage area is concentrated on a waist. When a massage is provided by changing volume of a sound and a frequency of a binaural beat in real time according to one embodiment of the present disclosure, it can be seen that concentration retention and concentration improvement are greater than those of a conventional massage.

For example, a golf mode may refer to a massage mode which relaxes muscles by intensively performing a tapping massage on areas such as a shoulder and a waist in relation to a massage position. In addition, a hip exercise mode may refer to a massage mode which induces tightening of a hip area by intensively applying kneading or acupressure (that is, a massage type) to a hip and a pelvis (that is, a massage position).

As described above, according to one embodiment of the present disclosure, based on a massage mode pre-stored according to a specific purpose, massage pattern information and/or audio information may be analyzed to change volume of a sound and a frequency of a binaural beat, which are provided together with a massage function, over time, thereby deriving a technical effect capable of maximizing a healing target value of a user, which is to be achieved in a corresponding mode.

In one embodiment of the present disclosure, when a massage mode input from a user is a concentration mode, a first step of a plurality of massage steps may include a step of changing a state of the user from an arousal state to a stable state, and a last step of the plurality of steps may include a step of changing the state of the user from the stable state to the arousal state.

As described above, in a concentration mode, for 15 minutes (i.e., during three steps), it is possible to induce a user from an arousal state to a first stable state and a second stable state in a manner similar to a sleep mode, and for the last 5 minutes (i.e., during a fourth step), it is possible to induce the user from a stable step to an arousal step. As described above, since a frequency of a binaural beat and volume of a sound are changed together for each step, it is possible to efficiently induce a user to a desired target state in a concept of a concentration mode. As a result, an optimal massage effect according to a desired mode may be provided to the user.

When a massage mode input from a user is a meditation mode, a first step of a plurality of massage steps may include a step of changing a state of a previous user from an arousal state to a stable state, and the remaining steps of the plurality of steps may include steps of inducing a state of the user to a deeper state as a step is changed to a next step.

As described in Table 2, in the case of the meditation mode, volume of a sound and a frequency of a binaural beat may be adjusted such that a sympathetic nerve overexcited for 30 minutes is relaxed and a mind and body are relaxed. In the meditation mode according to one embodiment of the present disclosure, as time passes, the state of the user may be induced to a more stabilized state by controlling the frequency of the binaural beat and the volume of the sound.

The steps shown in FIG. 9 are merely exemplary steps, and fewer or more steps may also be included in the scope of the present disclosure.

Points for distinguishing steps (for example, time stamps) may be indicated by 901, 902, 903, 904, and 905 in FIG. 9.

In order to achieve the same purpose (for example, the purpose of inducing a state of a user to a specific state), a frequency of a binaural beat and/or volume of a sound may be determined between the points. During each divided period, a frequency of a binaural beat and/or volume of a sound may be maintained in a constant state, and at a time point at which the divided period is changed, the frequency of the binaural beat and/or the volume of the sound may be changed.

As described above, amounts of changes in the frequency of the binaural beat and in the volume of the sound may be determined by comparing values before and after a change of a factor according to what the factor is changed at the change time point.

Figure 10:
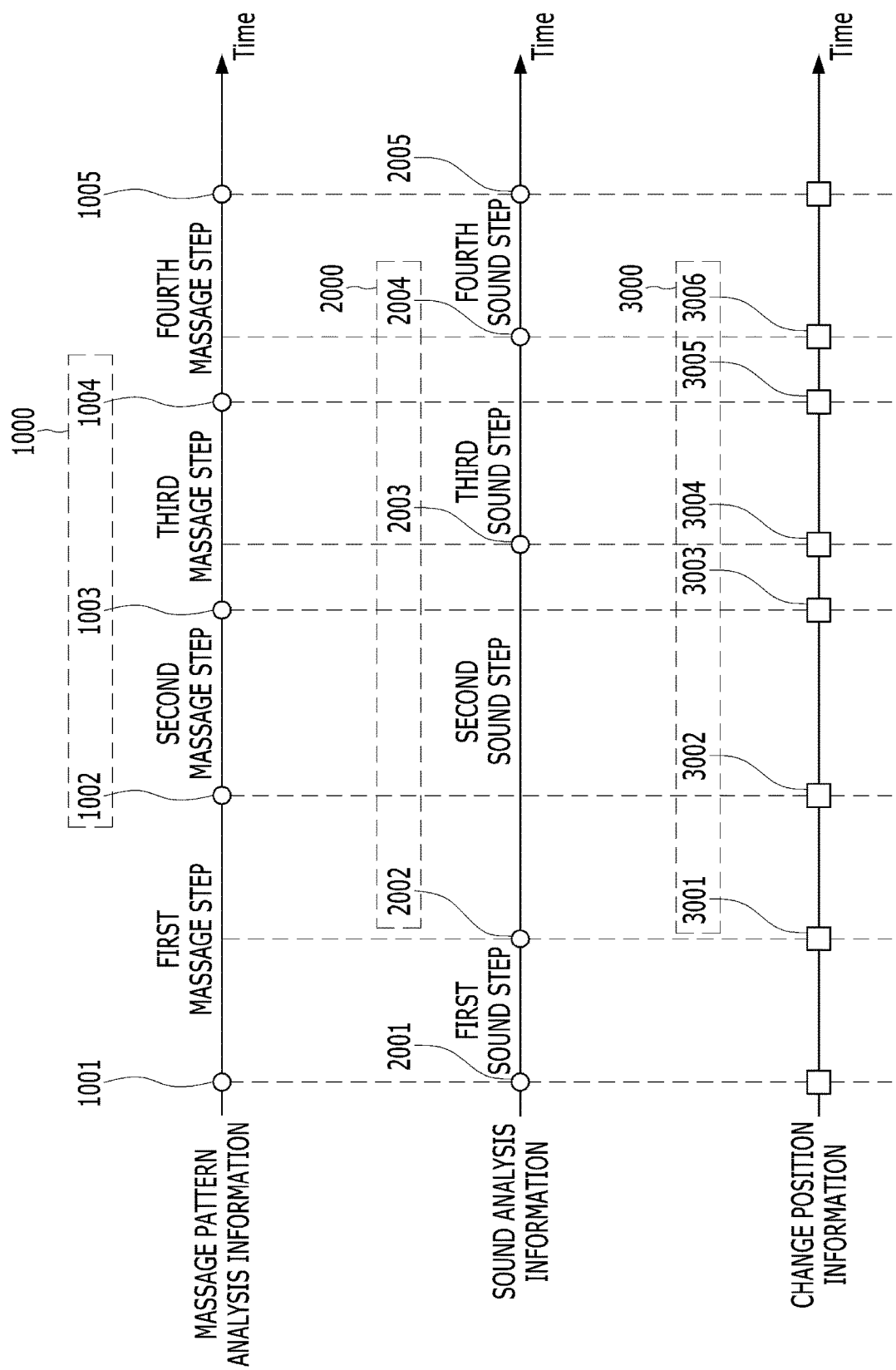
FIG. 10 illustrates an exemplary method of changing a frequency of a binaural beat and volume of a sound according to a specific massage mode according to one embodiment of the present disclosure.

FIG. 10 illustrates an exemplary method of changing a frequency of a binaural beat and volume of a sound according to a specific massage mode according to one embodiment of the present disclosure.

As shown in FIG. 10, massage pattern analysis information may include first time stamps 1000 (1002, 1003, and 1004) as points at which respective massage steps are changed. In addition, sound analysis information may include second time stamps 2000 (2002, 2003, and 2004) as points at which respective sound steps are changed. Here, the terms "first" and "second" are used to distinguish time stamps according to different factors. The first time stamps 1000 may include information related to time values with respect to points at which total massage time information (i.e., state information of a user according to a massage), massage type information, massage area information, and/or massage intensity information, which are included in the massage pattern analysis information, are changed. In addition, the second time stamps 2000 include information related to time values with respect to points at which music intensity information, music output time information, and music flow information, which are included in the sound analysis information, are changed.

In FIG. 10, the points 1001 and 2001 and the points 1005 and 2005 are illustrated as being start and end points and illustrated as not being time stamp points which are change points between steps. However, according to implementations, the start points such as the points 1001 and 2001 and the end points such as the points 1005 and 2005 may also become points to which time stamps, which are change points of volume of a sound and a frequency of a binaural beat, are allocated.

Based on the pieces of information about the time stamps 1000 and 2000, the massage device 100 may determine pieces of information about change points 3000 at which volume of a sound and/or a frequency of a binaural beat are to be changed. In an example in FIG. 10, volume of a sound and/or a frequency of a binaural beat may be changed at points 3001, 3002, 3003, 3004, 3005, and 3006.

In addition, the massage device 100 may determine what a changed factor is at each change point. For example, a first change point 3001 may refer to a point at which a first sound step is changed to a second sound step. The massage device 100 may identify what a change causative factor causes the first sound step to be changed to the second sound step based on the sound analysis information. For example, the change causative factor causing the first sound step to be changed to the second sound step according to the sound analysis information may be music intensity (for example, music intensity is changed from weak to strong). In this case, by comparing a scoring value of a frequency of a binaural beat and a scoring value of volume of a sound pre-allocated when music intensity is "weak" with a scoring value of a frequency of a binaural beat and a scoring value of volume of a sound pre-allocated when music intensity is "strong," the massage device 100 may determine how much to change the frequency of the binaural beat and the volume of the sound (that is, amounts of changes).

Figure 11:
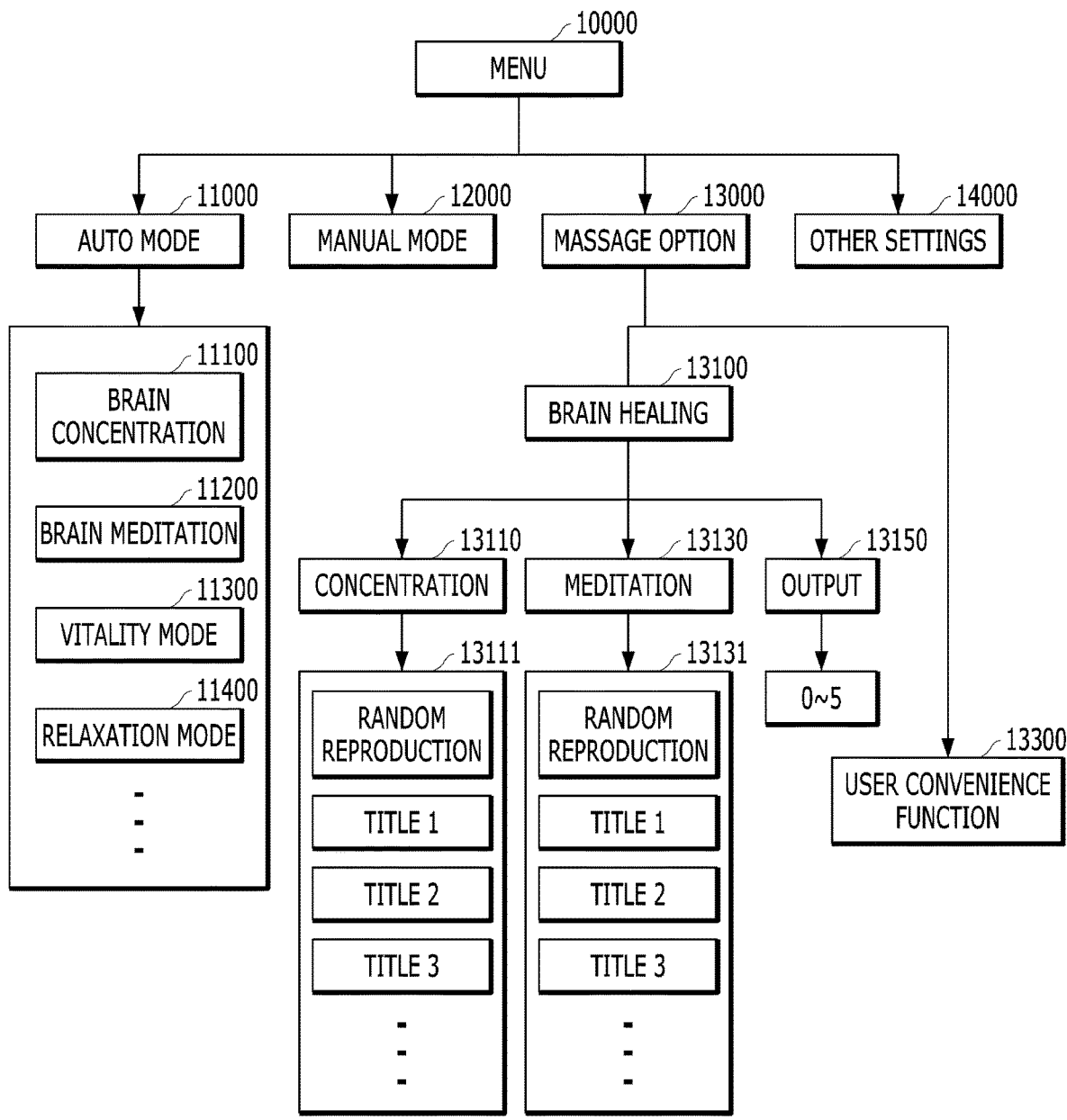
FIG. 11 is a schematic diagram of a menu configuration of the massage device according to one embodiment of the present disclosure.

FIG. 11 is a schematic diagram of a menu configuration of the massage device according to one embodiment of the present disclosure.

A menu 10000 of the massage device may include lower menus that may be connected according to a user input, and screen information corresponding to each menu may be displayed on the display 105. Hereinafter, each menu and screen information corresponding to each menu will be indicated by the same reference numeral. The menu 10000 of the massage device may include auto mode menu 11000, a manual mode menu 12000, a massage option menu 13000, and other settings menu 14000 as the lower menus. The menu configuration shown in FIG. 11 may show exemplary connection relationships of the lower menus that may be performed in a top menu according to a selection of a user. In the present disclosure, a menu including a lower menu may mean that, when a user selects a graphic object of a lower menu displayed on a screen including information about an upper menu, a screen may be converted into the lower menu corresponding to the graphic object selected in the upper menu. That is, the menu including the lower menu may mean that a user's menu search may proceed from an upper menu to a lower menu.

The auto mode menu 11000 is a menu associated with a function of executing an auto massage mode including a predetermined massage pattern and massage time. The auto mode menu 11000 is a menu in which modes, in which an operation time of the massage device and a massage pattern are pre-appointed, are collected so as to provide a massage to a user without an additional operation. The auto mode menu 11000 may include, for example, a brain concentration mode, a brain meditation mode, a recovery mode, a vitality mode, a stretching mode, a sleep mode, a vitality mode, a golf mode, an examinee mode, a hip exercise mode, an upper body auto mode, a lower body auto mode, a care mode, a lymphatic massage mode, a digestive mode, a hangover cure mode, a rapid growth mode, a zero gravity mode, and the like, but the above-described massage modes are merely examples and the present disclosure is not limited thereto. The user may operate a massage function of a massage pattern pre-stored in the massage device by selecting the auto mode menu 11000 and selecting a massage mode which is a lower mode.

The brain concentration mode may be a type of brain massage mode which improves a brain function by inducing brain wave synchronization using healing music such as a binaural beat and a mechanical massage of the massage device 100 and may be a brain massage mode which improves concentration of a user.

The brain meditation mode may be a type of brain massage mode which improves a brain function by inducing brain wave synchronization using healing music such as a binaural beat and a mechanical massage of the massage device 100 and may be a brain massage mode which induces a brain of a user to enter a comfortable state. The brain concentration mode and the brain meditation mode may include a mechanical massage mode such as a recovery mode as a lower menu.

The recovery mode may be a massage mode which intensively provides an acupressure massage to a shoulder, a back, and a waist of a user.

The stretching mode may be a full body massage mode which stretches each area of a whole body of a user to relax muscles in a state in which the whole body of the user is fixed using air pressure control of the massage module 102. In this case, the massage module 102 fixing a leg of the user and the massage module 102 fixing an upper body of the user may be moved at different angles to stretch the body of the user.

The sleep mode may be a full body massage mode which induces sleep of a user while a massage type is changed from a massage pattern concentrated on tapping with respect to a massage area of a back to a massage pattern concentrated on kneading and acupressure over time.

The vitality mode may be a massage mode which enhances vitality of a user by intensively providing tapping and kneading to a shoulder of a user.

The golf mode may be a full body massage mode which relaxes muscles tightened due to exercise and may be a massage mode which provides an intensive tapping massage to a shoulder and effectively relaxes all muscles of the body while an angle of the body structure 101 is automatically adjusted in 3 steps.

The examinee mode may be a waist massage-concentrated course for an examinee who sits for a long time and may be a full body massage mode which mainly includes acupressure and tapping massage patterns performed on an area from an upper end to a lower end of a waist.

The hip exercise mode may be a full body massage mode which induces tightening of a hip area by intensively providing kneading, acupressure, and air massages to a hip and a pelvis of a user.

The upper body auto mode may be a massage mode which is focused on an upper body by intensively providing kneading, acupressure, and air massages to a shoulder and a back of a user.

The lower body auto mode may be a massage mode which is focused on a lower body by intensively providing kneading, acupressure, and air massages to a leg and a pelvis of a user.

The care mode may be a relaxation massage mode which relaxes muscles tightened in a shoulder and a waist of a user through acupressure and tapping.

The lymphatic massage mode may be a massage mode which assists in lymphatic circulation of a user by controlling the body structure 101 to lift a leg of the user and providing a special type of kneading using air pressure to an arm and the leg of the user.

The digestive mode may be a massage mode which assists in digestion of a user by intensively stimulating acupoints which are present in a back of the user to assist in digestion and presses an arm and a leg of the user to allow blood to flow toward a digestive system.

The hangover cure mode may be a massage mode which assists in stabilizing a digestive system of a user by intensively stimulating acupoints which are present in a back of the user to assist in digestion and presses an arm and a leg of the user to allow blood to flow toward the digestive system.

The rapid growth mode may be a massage mode including operations of the massage module 102, which relieves growing pains of a user corresponding to infancy or adolescence and assists in growth of the user.

The zero gravity mode may be a massage mode which adjusts an angle of the body structure accommodating a body of a user to implement the most comfortable posture at which the gravity applied to a user is minimized.

The manual mode menu 12000 may be a menu associated with a function of executing a manual mode which allows a user to set a massage pattern and a massage time.

The massage option menu 13000 may be a menu associated with a function of selecting a massage option mode including an additional function of finely adjusting a predetermined massage pattern of the massage device. The massage option menu 13000 may include a brain healing output menu 13100 and a user convenience function menu 13300.

The brain healing output menu 13100 may include menus 13110 and 13130 for selecting a type of healing music such as a binaural beat for a brain massage and an output intensity selection menu 13150 for selecting output intensity. A brain healing output for a brain massage may include healing music such as a binaural beat, a lighting effect, and the like, and the scope of the present disclosure is not limited to a type of the brain healing output. The brain healing output menu 13100 may include a brain concentration menu 13110, a brain meditation menu 13130, and the output intensity menu 13150.

The brain concentration menu 13110 may be a menu associated with a function of selecting an output of the massage device 100 for a brain massage which increases concentration of a user. The brain concentration menu 13110 may be, for example, a menu associated with a function of selecting a sound output related to concentration.

The brain meditation menu 13130 may be a menu associated with a function of selecting an output of the massage device 100 for a brain massage for a brain of a user to rest. The brain meditation menu 13130 may be, for example, a menu associated with a function of selecting a sound output related to a brain rest.

The output intensity menu 13150 may be a menu associated with a function for selecting output intensity of the massage device 100 for a brain massage. The output intensity menu 13150 may be, for example, a menu associated with a function of adjusting intensity of a sound output for a brain massage.

The user convenience function menu 13300 may be a menu associated with a function of finely controlling a massage pattern. The user convenience function menu 13300 may be, for example, a menu associated with functions of adjusting rolling intensity of the massage module 102 and a temperature of a heating function of the massage device 100 and adjusting a rolling speed of the massage module 102 and intensity of an airbag massage of the massage module 102 and may include a lower menu for adjusting each function.

The other settings menu 14000 may be a menu associated with a function of adjusting a function for user convenience other than a function of applying a massage to at least a part of a body of a user of the massage device 100. For example, the other settings menu 14000 may be a menu associated with a function of setting a Bluetooth connection, input lock, help, a device display language, and the like. That is, the other settings menu 14000 may be a menu associated with a function of controlling all operations other than a massage operation of the massage device 100.

A user may select respective menus by operating the input unit 104. For example, the user may select respective menus by operating buttons of the input unit 104, and the user may select respective menus displayed on the display 105 by operating a touch screen of the input unit 104. The present disclosure is not limited by a menu selection method of a user.

Figure 12:
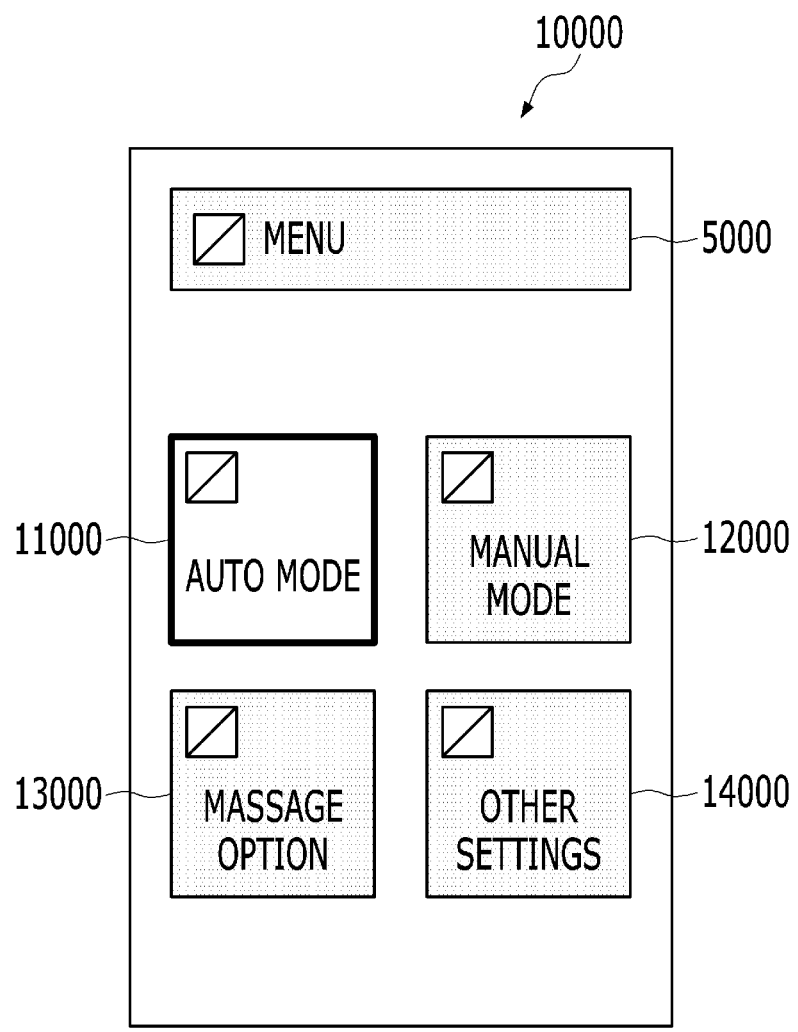
FIG. 12 is a schematic diagram of a top menu screen displayed on a display of the massage device according to one embodiment of the present disclosure.

FIG. 12 is a schematic diagram of a top menu screen displayed on the display of the massage device according to one embodiment of the present disclosure.

When the massage device 100 is operated, a top menu screen 10000 shown in FIG. 12 may first be displayed on the display 105. In the top menu screen 10000 shown in FIG. 12, graphic objects 11000, 12000, 13000, and 14000 of lower menus are illustrated as being displayed in the form of 2 by 2, but this is merely an example. In the top menu screen 10000, the graphic objects of the lower menus may be displayed in various display forms such as the form of 3 by 3. The example of the top menu screen 10000 shown in FIG. 12 may be an example of a state in which an auto mode graphic object 11000 is focused.

The top menu screen 10000 may include screen information indicating a massage mode selectable by a user of the massage device. The screen information about the massage mode may include an auto mode graphic object 11000 associated with a function of executing an auto mode including a predetermined massage pattern and massage time, a manual mode graphic object 12000 associated with a function of allowing a user of the massage device to set a massage pattern and a massage time, a massage option mode graphic object 13000 associated with a function of selecting a massage option mode including an additional function of finely adjusting the predetermined massage pattern of the massage device, an other settings graphic object 14000 associated with a function related to other settings, and a menu state graphic object 5000 indicating a current menu state.

When an input with respect to a graphic object is received from a user on the basis of an input of the input unit 104, the control unit 205 may determine to execute a function associated with the graphic object.

An example shown in FIG. 12 refers to a case in which a cursor is positioned on the auto mode graphic object 11000. In a state in which the example shown in FIG. 12 is displayed on the display 105, when a user input with respect to the graphic object 11000, 12000, 13000, or 14000 associated with a function related to a lower menu is received from a user, the control unit 205 may determine to convert screen information into a function associated with a corresponding graphic object.

Figure 13:
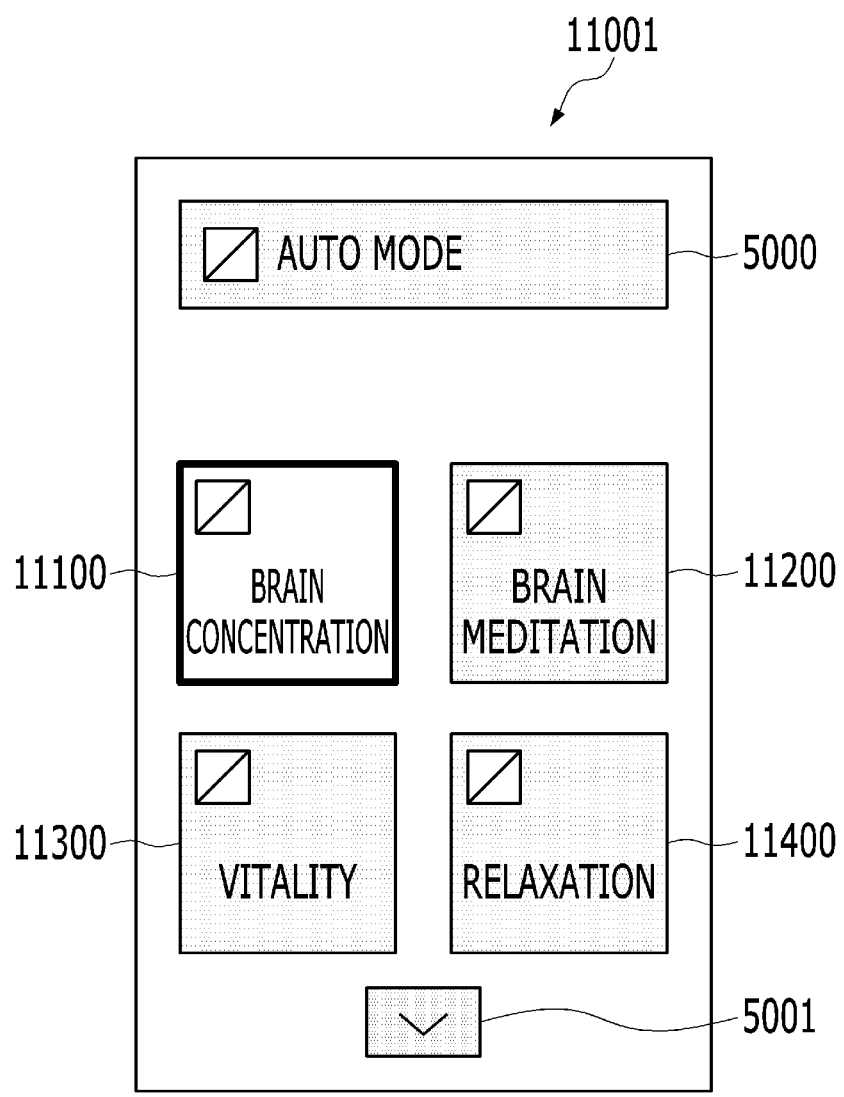
FIG. 13 is a schematic diagram of a lower menu screen displayed on the display of the massage device according to one embodiment of the present disclosure.

FIG. 13 is a schematic diagram of a lower menu screen displayed on the display of the massage device according to one embodiment of the present disclosure.

FIG. 13 is a schematic exemplary diagram illustrating that auto mode screen information 11001 is displayed on the display according to one embodiment of the present disclosure. In a state in which the top menu screen 10000 is displayed, when the input unit 104 receives an input with respect to the auto mode graphic object 11000 from a user, the auto mode screen information 11001 shown in FIG. 13 may be displayed on the display. In a state in which massage mode screen information 10000 is displayed on the display 105, when the input unit 104 receives the input with respect to the auto mode graphic object 11000 from the user, the control unit 205 may determine to display the auto mode screen information 11001 on the display 105. A menu state graphic object 5000 may indicate that a menu being displayed is an auto mode menu. An example of the auto mode screen information 11001 shown in FIG. 13 may be an example of a state in which a brain concentration mode graphic object 11100 is focused.

The auto mode screen information 11001 may include massage pattern graphic objects 11100, 11200, 11300, and 11400 associated with functions of executing one or more predetermined massage patterns. In an example of FIG. 13, the graphic objects are illustrated as being displayed in the form of 2 by 2, but this is merely an example. The present disclosure may include various methods of displaying graphical objects. The massage pattern graphic objects may include one or more graphic objects associated with a function of executing predetermined massage patterns. The example of FIG. 13 includes the brain concentration mode graphic object 11100, a brain meditation mode graphic object 11200, a vitality mode graphic object 11300, and a relaxation mode graphic object 11400, but all massage modes of the massage device 100 may be displayed as graphic objects. A scrolling graphic object 5001 may be displayed at a lower end of the display so as to indicate that other massage modes may be displayed other than the graphic objects 11100, 11200, 11300, and 11400 which are being displayed. As described above, the massage device 100 of the present disclosure may have various massage patterns in addition to the massage patterns shown in FIG. 13. The massage patterns are not displayed as graphic objects in FIG. 13, but graphic objects associated with functions of the massage patterns may be displayed.

Figure 14:
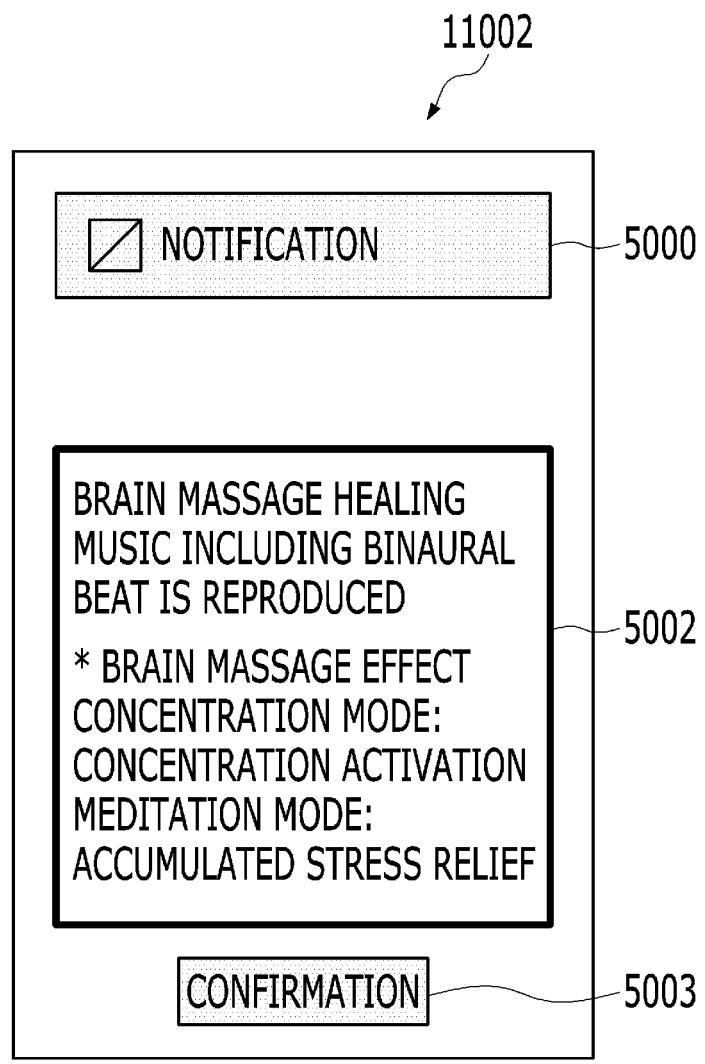
FIG. 14 is a schematic diagram of a notification screen displayed on the display of the massage device according to one embodiment of the present disclosure.

FIG. 14 is a schematic diagram of a notification screen displayed on the display of the massage device according to one embodiment of the present disclosure.

FIG. 14 is an exemplary diagram illustrating that brain massage notification screen information 11002 is displayed on the display 105 according to one embodiment of the present disclosure. In a state in which the auto mode screen information 11001 is displayed, when an input with respect to the brain concentration mode graphic object or brain meditation mode graphic object (i.e., a graphic object associated with a function related to a brain massage) is received from a user, the brain massage notification screen information 1102 shown in FIG. 14 may be displayed on the display.

In a state in which the auto mode screen information 11001 is displayed on the display 105, when the input unit 104 receives the input with respect to the brain concentration mode graphic object or brain meditation mode graphic object from the user, the control unit 205 may determine to display the massage notification screen information on the display 105. The brain massage notification screen information 11002 may be screen information for notifying that a massage mode selected by a user is a mode including a brain massage.

The brain massage notification screen information 11002 may include a notification graphic object 5002 for notifying a user that a brain massage mode, which includes healing music including a binaural beat and a massage of the massage device, is performed, and a progress graphic object 5003 associated with a function of proceeding to a step of executing a selected massage pattern. The notification graphic object 5002 may include information for notifying the user that the brain massage is performed, details of the brain massage, and contents related to effects of the brain massage.

The brain massage notification screen information 11002 may be displayed when the user selects the brain massage and thus may notify the user that a corresponding massage mode includes the brain massage mode other than a mechanical massage of the massage device 100.

When the input unit 104 receives an input with respect to the progress graphic object 5003 from the user, the control unit 205 may perform a process of executing a massage operation. For example, the control unit 205 may determine a body shape of the user based on signals received from one or more sensors of the body structure 101 and may control movement of the massage module 102 based on the determined body shape of the user to execute a massage mode. For example, in this case, the control unit 205 may determine to display body shape determination screen information 11002, which indicates that the massage device 100 is determining the body shape of the user, on the display 105.

Figure 15:
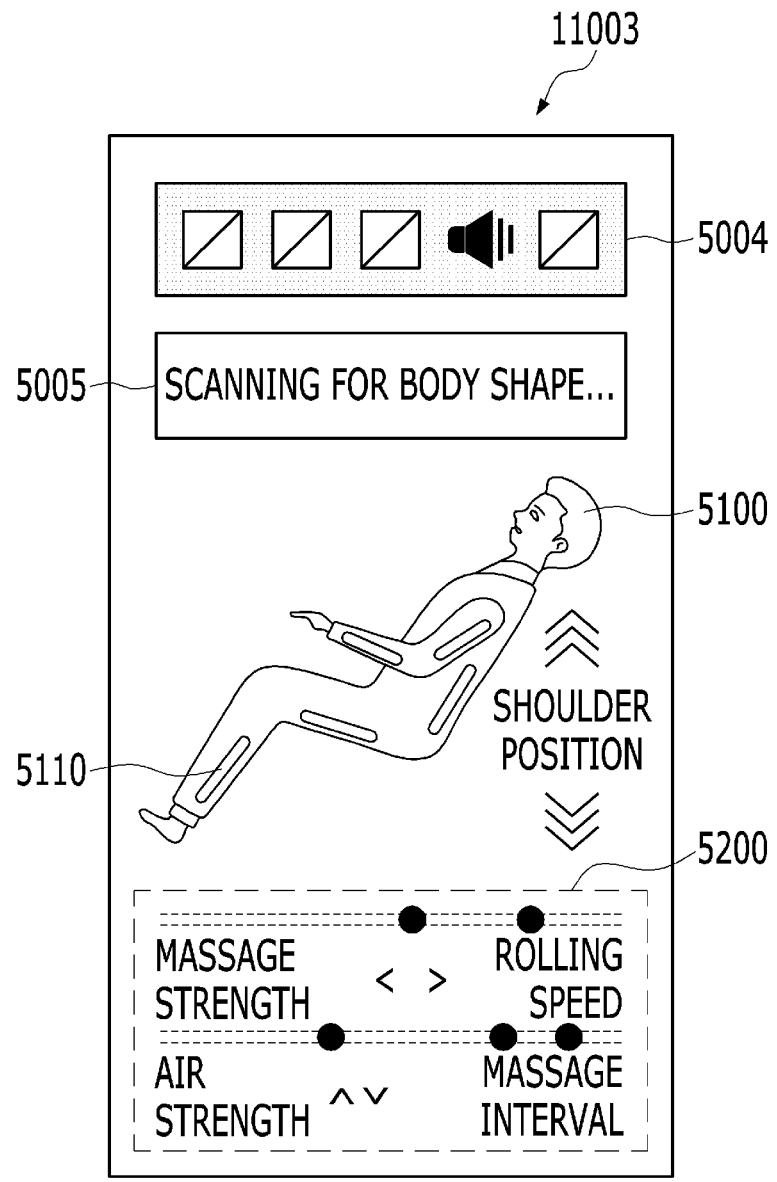
FIG. 15 is a schematic diagram of a user body shape determination screen displayed on the display of the massage device according to one embodiment of the present disclosure.

FIG. 15 is a schematic diagram of a user body shape determination screen displayed on the display of the massage device according to one embodiment of the present disclosure.

When the input unit 104 receives a user input with respect to a massage pattern graphic object from a user, body shape determination screen information 11003 may be displayed on the display 105. In addition, in a state in which the brain massage notification screen information 11002 is displayed, when the input unit 104 receives a user input with respect to the progress graphic object 5003 from the user, the body shape determination screen information 11003 may be displayed on the display 105. The body shape determination screen information 11003 may be displayed on the display 105 between time points of a selection of a massage mode by the user and execution of the massage mode in addition to the above-described cases.

The body shape determination screen information 11003 may include a user shape graphic object 5100 and a massage setting graphic object 5200. Additionally, the body shape determination screen information 11003 may further include a current massage option graphic object 5004 indicating an operation of a user convenience function and a current massage mode graphic object 5005 indicating an operation mode and operation state of the massage device 100.

The user shape graphic object 5100 may indicate a user of the massage device. The user shape graphic object 5100 may include a massage position graphic object 5110 indicating a part of a body of a user corresponding to a position at which the massage module is disposed. The massage position graphic object 5110 may distinguish and indicate each part of the body of the user, to which a massage of the massage device 100 may be provided. For example, the massage device 100 may provide a calf massage, a thigh massage, a waist massage, an arm massage, a shoulder massage, and the like, and the massage position graphic object 5110 may distinguish and indicate each part of the body of the user. The massage position graphic object 5110 may be selected for each part, and in this case, the massage position graphic object 5110 may be associated with a function of adjusting massage setting of each selected part. In a state in which the specific massage position graphic object 5110 is selected, when the input unit 104 receives an input with respect to any point on a user shape graphic object 5100, which does not correspond to the massage position graphic object 5110, the control unit 205 may determine that an entire massage area is selected and thereby determine to change the massage setting graphic object 5200 into information related to the entire massage area.

The massage setting graphic object 5200 may be associated with a function of displaying information related to operation of the massage module and adjusting the operation of the massage module. The massage setting graphic object 5200 may display operation intensity, an operation speed, airbag intensity, a massage interval, and the like of the massage module. The massage setting graphic object 5200 may display information related to overall operations of the massage module, or when the user selects the massage position graphic object 5110, the massage setting graphic object 5200 may display information related to operation of the massage module with respect to a selected part. For example, the massage setting graphic object 5200 may display information related to the operation of the massage module with respect to a whole body or may display information related to the operation of the massage module which is related to a thigh area. When the input unit 104 receives a user input with respect to the massage position graphic object 5110, the control unit 205 may determine to display a massage setting, which corresponds to the massage module disposed at a position corresponding to the selected massage position graphic object 5110, on the massage setting graphic object 5200. When the user selects the massage position graphic object 5110, the massage setting graphic object 5200 may be changed to information related to the operation of the massage module with respect to a selected area. The massage setting graphic object 5200 may be associated with a function of a setting operation of the massage module, and when the input unit 104 receives an input of setting the operation of the massage module, the control unit 205 may change the operation of the massage module in response to the user input. For example, the user may adjust massage intensity by operating the massage setting graphic object 5200. The above-described massage setting is merely an example, and the present disclosure is not limited thereto.

The current massage option graphic object 5004 may indicate an operation of a user convenience function. In an example shown in FIG. 15, a speaker shape of the current massage option graphic object 5004 may indicate that a music function is being output. In addition, the current massage option graphic object 5004 may indicate whether the user convenience function is operated, an operation state of the user convenience function, or the like, such as whether a heating function is operated.

The current massage mode graphic object 5005 may indicate an operation mode and an operation state. In the example shown in FIG. 15, since the body shape determination screen information 11003 is being displayed, the current massage mode graphic object 5005 may indicate that the massage device 100 is determining a body shape of the user.

When the determination of the body shape of the user is completed, the control unit 205 may determine to display operation screen information 11004.

Figure 16:
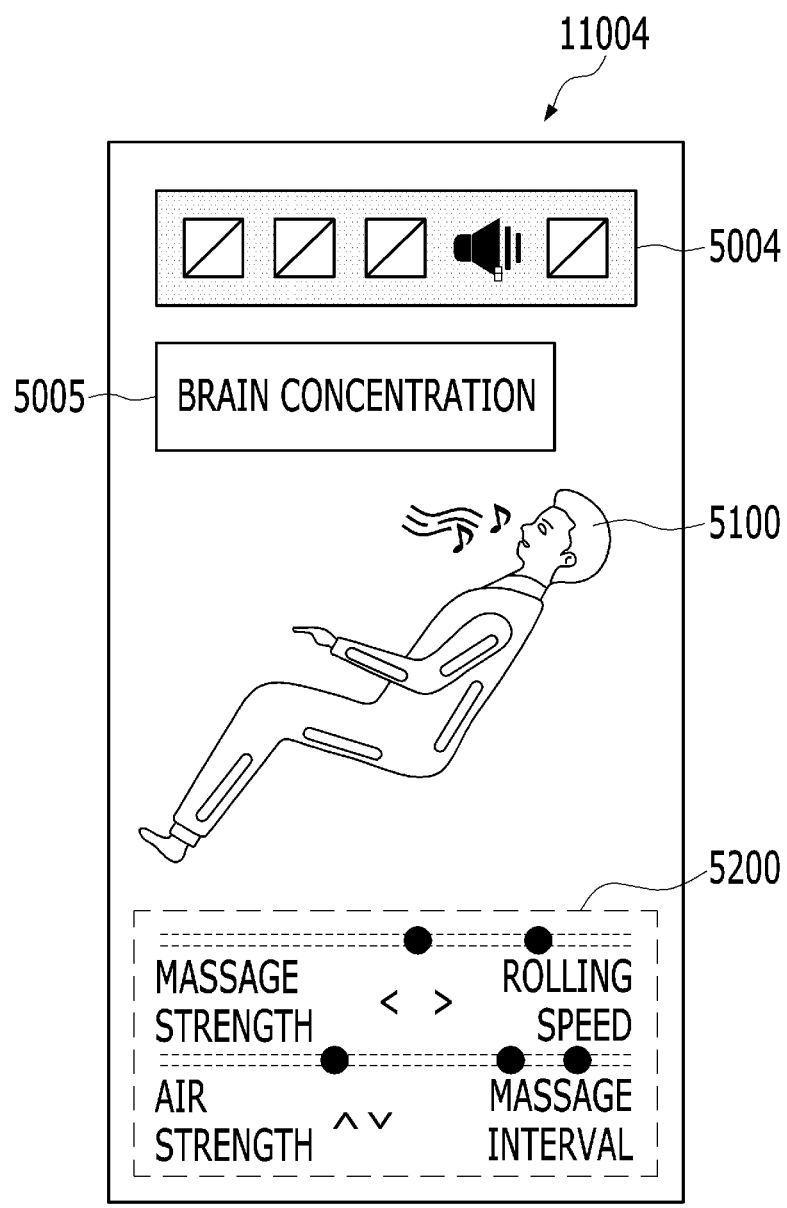
FIG. 16 is a schematic diagram of an operation screen displayed on the display of the massage device according to one embodiment of the present disclosure.

FIG. 16 is a schematic diagram of an operation screen displayed on the display of the massage device according to one embodiment of the present disclosure.

The operation screen information 11004 may be displayed on the display 105 while the massage device 100 provides a massage function to a user. The operation screen information 11004 may include information indicating a massage operation state of the massage device. The operation screen information 11004 may include the user shape graphic object 5100, the massage setting graphic object 5200, the current massage mode graphic object 5005, and the current massage option graphic object 5004. Since the functions of the user shape graphic object 5100, the massage setting graphic object 5200, the current massage mode graphic object 5005, and the current massage option graphic object 5004 are the same as those described with reference to FIG. 15, descriptions thereof will be omitted.

Figure 17:
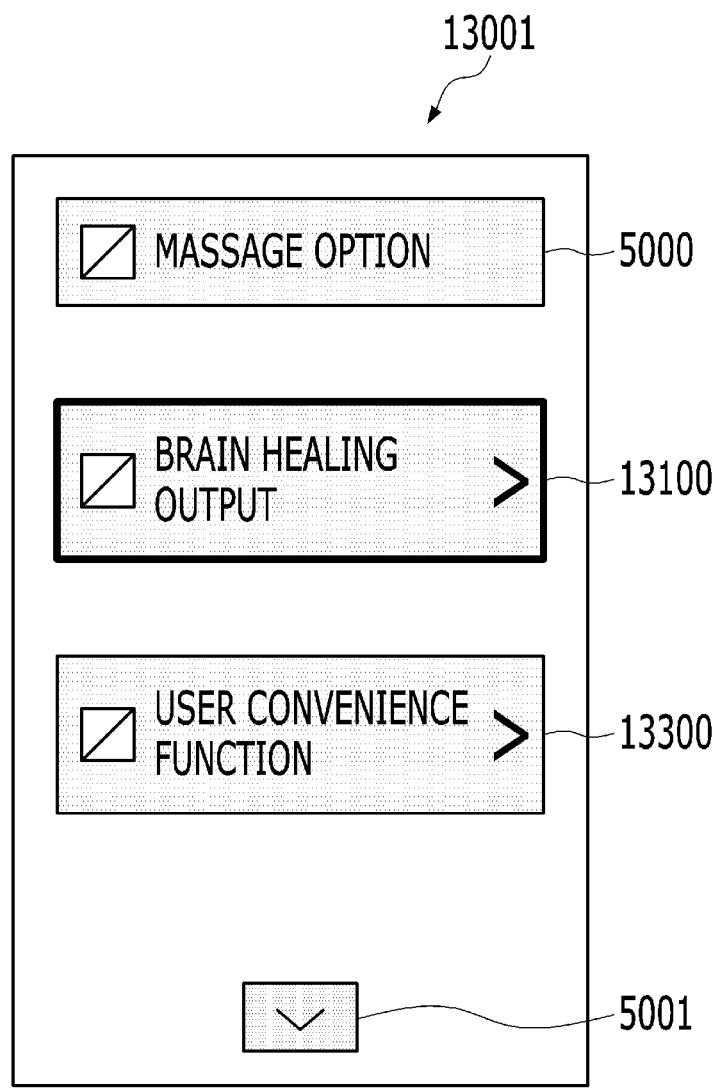
FIG. 17 is a schematic diagram of a lower menu screen displayed on the display of the massage device according to one embodiment of the present disclosure.

FIG. 17 is a schematic diagram of a lower menu screen displayed on the display of the massage device according to one embodiment of the present disclosure.

In a state in which the top menu screen 10000 is displayed, when the input unit 104 receives an input with respect to the massage option mode graphic object 13000 from a user, massage option mode screen information 13001 shown in FIG. 17 may be displayed on the display. When the input unit receives the input with respect to the massage option mode graphic object 13000 from the user, the control unit 205 may determine to display the massage option mode screen information 13001 on the display.

The massage option mode screen information 13001 may include a brain massage setting graphic object 13100 and a user convenience function setting graphic object 13300. In addition, the massage option mode screen information 13001 may further include a menu state graphic object 5000 and a scrolling graphic object 5001 associated with a scrolling function.

The brain massage setting graphic object 13100 may be a graphic object associated with a function of outputting screen information 13002, through which a function of a brain massage may be set. The setting of the function of the brain massage may include setting of an output type and output intensity for the brain massage. When the input unit 104 receives an input with respect to the brain massage setting graphic object 13100 from the user, the control unit 205 may determine to display brain massage function screen information 13002, which may set the function of the brain massage, on the display. When a user input with respect to the brain massage setting graphic object 13100 is received, the display 105 may be converted into the brain massage function screen information 13002.

The user convenience function setting graphic object 13300 may be a graphic object corresponding to the user convenience function menu 13300. The user convenience function setting graphic object 13300 may be, for example, a graphic object associated with functions of adjusting rolling intensity of the massage module 102 and a temperature of a heating function of the massage device 100 and adjusting a rolling speed of the massage module 102 and intensity of an airbag massage of the massage module 102. The user convenience function setting graphic object 13300 may be displayed as a single graphic object including a lower menu as in an example shown in FIG. 17 and may also be displayed as a plurality of graphic objects associated with functions included in lower menus of the user convenience function menu. That is, for example, the user convenience function setting graphic object 13300 may be displayed as graphic objects, such as a graphic object associated with heating function setting and a graphic object associated with rolling speed setting of the massage module.

Figure 18:
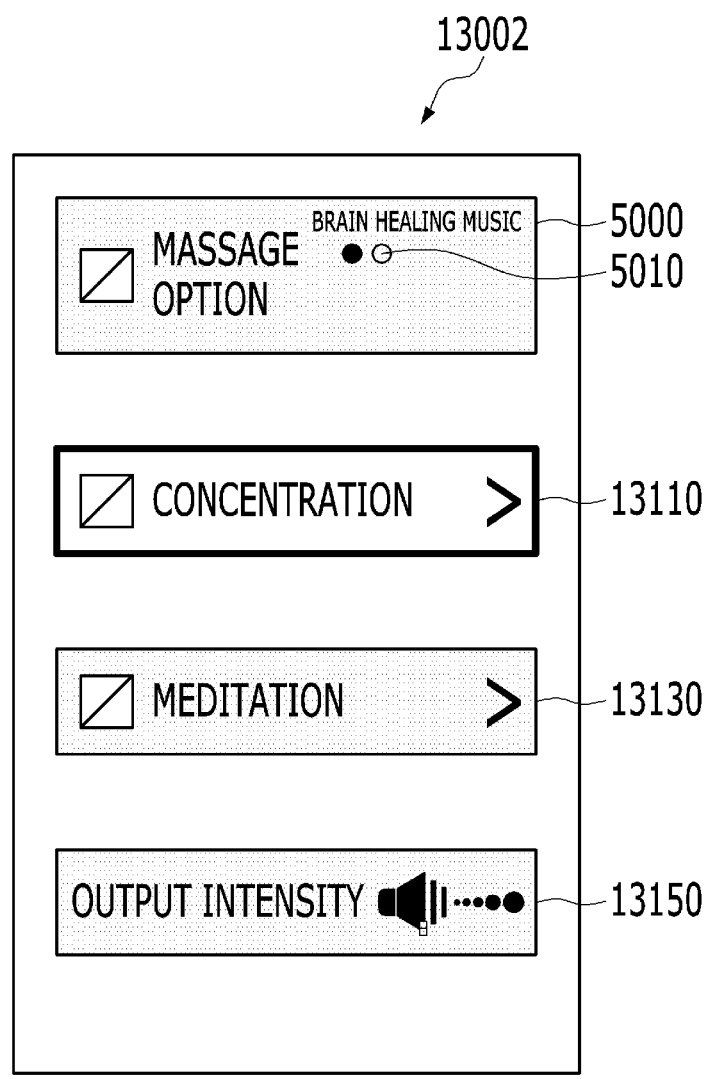
FIG. 18 is a schematic diagram of a lower menu screen displayed on the display of the massage device according to one embodiment of the present disclosure.

FIG. 18 is a schematic diagram of a lower menu screen displayed on the display of the massage device according to one embodiment of the present disclosure.

In a state in which the massage option mode screen information 13001 is displayed, when the input unit 104 receives an input with respect to the brain massage setting graphic object 13100 from a user, brain massage function screen information 13002 shown in FIG. 18 may be displayed on the display. When the input unit 104 receives the input with respect to the brain massage setting graphic object 13100 from the user, the control unit 205 may determine to display the brain massage function screen information 13002 on the display.

The brain massage function screen information 13002 may include a menu for setting a function of a brain massage. The brain massage function screen information 13002 may include brain healing output selection graphic objects 13110 and 13130 and a brain healing output intensity selection graphic object 13150. The brain massage function screen information 13002 may additionally include a menu state graphic object 5000 and may include an index graphic object 5010 indicating that a current menu is a menu for setting the function of the brain massage. The index graphic object 5010 may be configured to indicate a depth of a menu.

The brain healing output selection graphic objects 13110 and 13130 may be graphic objects associated with a function of selecting a type of brain healing output of the brain massage. In an example shown in FIG. 18, the brain healing output is illustrated as being the graphic object 13110 associated with a function of determining an output related to a concentration mode and as being the graphic object 13130 associated with a function of determining an output related to a meditation mode, but the present disclosure is not limited thereto. When the input unit 104 receives an input with respect to the brain healing output selection graphic object 13110 or 13130 from a user, the control unit 205 may determine to display brain healing output detailed-type selection screen information 13003 on the display such that a detailed type of selected brain healing output is selected. For example, when the user selects the graphic object 13110 associated with the function of determining the output related to the concentration mode, the control unit 205 may determine to display the brain healing output detailed-type selection screen information 13003 on the display such that the user selects a detailed output of the output related to the concentration mode.

Figure 19:
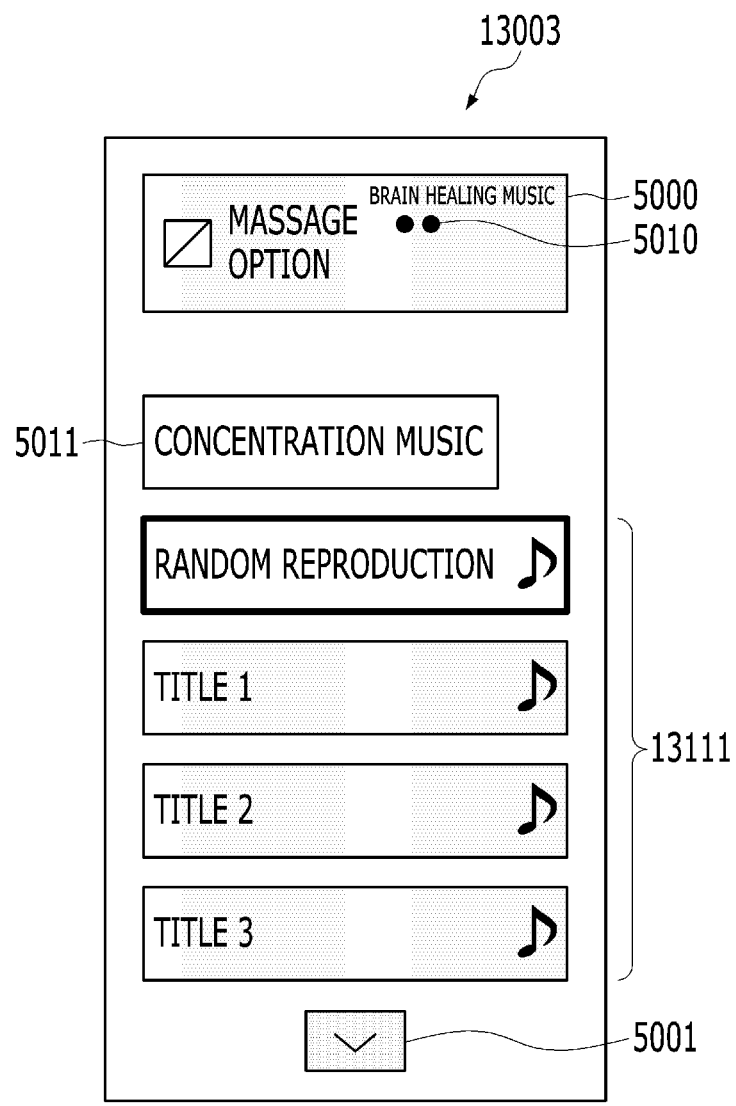
FIG. 19 is a schematic diagram of a lower menu screen displayed on the display of the massage device according to one embodiment of the present disclosure.

FIG. 19 is a schematic diagram of a lower menu screen displayed on the display of the massage device according to one embodiment of the present disclosure.

In a state in which the brain massage function screen information 13002 is displayed, the brain healing output detailed-type selection screen information 13003 shown in FIG. 19 may refer to an example of a screen displayed when the input unit 104 receives an input with respect to the graphic object 13110 of the brain healing output selection graphic objects 13110 and 13130, which is associated with the function of determining the output related to the concentration mode, from a user. When the input unit 104 receives an input with respect to the brain healing output selection graphic object 13110 or 13130 from the user, the control unit 205 may determine to display the brain healing output detailed-type selection screen information 13003 on the display such that a detailed type of selected brain healing output is selected.

The brain healing output detailed-type selection screen information 13003 may include a menu for selecting the detailed type of the selected brain healing output. The brain healing output detailed-type selection screen information 13003 may include a brain healing output detailed-type graphic object 13111 associated with a function of selecting the detailed type of the brain healing output. The brain healing output detailed-type selection screen information 13003 may additionally include a menu state graphic object 5000, a scrolling graphic object 5001, and an index graphic object 5010 configured to indicate a depth of a current menu. In addition, the brain healing output detailed-type selection screen information 13003 may additionally include a brain healing output display graphic object 5011 for displaying a type of the selected brain healing output.

When the user selects each graphic object of the brain healing output detailed-type graphic object 13111, the control unit 205 may generate an output based on the selected graphic object. For example, when the user selects random reproduction, the control unit 205 may determine to randomly reproduce a pre-stored sound output related to concentration. In this case, the control unit 205 may output screen information associated with a function of adjusting a sound of an output.

The massage device 100 according to one embodiment of the present disclosure may provide a voice output for a brain massage and may simultaneously perform a massage mode operation and a voice output operation of the massage device 100, thereby improving immediacy and convenience of a user operation.

According to one embodiment of the present disclosure, changes in volume of a sound and in a frequency of a binaural beat and amounts of the changes may be achieved in real time according to characteristics of an auto massage mode provided by a massage chair, thereby providing an optimal healing sound to a user and concurrently optimizing an effect of a massage function.

Those skilled in the art of the present disclosure will appreciate that information, signals, and data may be expressed using any of a variety of different technologies and techniques. For example, data, information, commands, signals, bits, symbols, and chips which may be referred to in the above descriptions may be expressed by voltages, currents, electromagnetic waves, magnetic fields or particles, optical fields or particles, or any combination thereof.

Those skilled in the art of the present disclosure will appreciate various exemplary logic blocks, modules, processors, means, circuits, and algorithm steps can be implemented by electronic hardware, various types of programs or design codes (referred to as "software" herein for convenience), or a combination thereof described in association with the embodiments disclosed herein. In order to clearly describe the intercompatibility of the hardware and the software, various exemplary components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but such implementation decisions should not be interpreted as causing a departure from the scope of the present disclosure.

Various exemplary operations, logic blocks, modules, and circuits described in association with the embodiments disclosed herein may be used interchangeably with each other and may be implemented or performed by a general processor, a digital signal processor (DSP), an application specific integrated circuit (ASIC), a field programmable gate array (FPGA) or another programmable logic device, a discrete gate or transistor logic, discrete hardware components, or any combination thereof designed to perform the functions described herein. A general purpose processor may be a microprocessor, but in the alternative, the general processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

It will be appreciated that a specific order or a hierarchical structure of steps in the presented processes and methods is one example of exemplary accesses. It will be appreciated that the specific order or the hierarchical structure of the steps in the processes within the scope of the present disclosure may be rearranged based on design priorities. Appended method claims provide elements of various steps in a sample order, but this does not mean that the method claims are limited to the presented specific order or hierarchical structure.

Steps of a method or an algorithm described in association with the embodiments disclosed in the specification may be directly implemented by hardware, a software module executed by a processor, or a combination thereof. The software module (including, for example, executable commands and related data) and other data may be stored in a RAM, a flash memory, a ROM, an EPROM, an EEPROM, registers, a hard disk, a movable disk, a CD-ROM, or a data memory (for example, a computer-readable medium) such as any other form of storage medium which is technologically known. An exemplary storage medium may be connected to a machine such as a computer or processor (which may be referred to as a "processor" for convenience), and as a result, the processor may read information (for example, software commands) from a storage medium and may record information in the storage medium. Exemplary storage media may be integrated into a processor. A processor and a storage medium may be included in an ASIC. The ASIC may be included in a user device. Alternatively, the processor and the storage medium may be included in the user device as separate components.

In one or more exemplary designs, described technologies may be implemented by hardware, software, firmware, or any combination thereof. When the technologies are implemented by software, functions may be stored or coded in a computer-readable medium. The computer-readable medium includes both a computer-readable storage medium and a computer-readable transmission medium including any medium that facilitates transmission of a computer program from one place to another place. The computer-readable storage medium may be any usable medium which may be accessed by a general or special purpose computer. As an example, without limitation, the computer-readable storage medium may be accessed by a RAM, a ROM, an EEPROM, a CD-ROM, another optical disk storage, a magnetic field disk storage, other magnetic field storage devices, a general or special purpose computer, or a general or special purpose processor and may include any other medium which may be used to transport or store program code means required in the form of indications or data structures. As another example, when software is transmitted from a website, a server, or another remote source by using a coaxial cable, an optical fiber cable, a twist pair, a digital subscriber line (DSL), or wireless technologies such as infrared ray transmission, wireless transmission, and microwave transmission, the coaxial cable, the optical fiber cable, the twist pair, the DSL, or the wireless technologies such as wireless technologies, such as infrared ray transmission, wireless transmission, and microwave transmission are included in a definition of a computer-readable storage medium. As used herein, a disk and a disc include a compact disk (CD), a laser disk, an optical disk, a digital video disk (DVD), a floppy disk, and a blue-ray disk. Here, the disks optically reproduce data with a laser, while the disks generally magnetically reproduce data. Combinations of those described above will also be included in the range of the computer-readable medium The description of the presented embodiments is provided so that those skilled in the art of the present disclosure may use or implement the present disclosure. Various modifications of the embodiments will be apparent to those skilled in the art of the present disclosure, and general principles defined herein can be applied to other embodiments without departing from the scope of the present disclosure. Therefore, the present disclosure is not limited to the embodiments presented herein but should be interpreted within the widest range which is associated with the principles and new features presented herein.

The invention claimed is:

1. A massage device comprising:
a body structure comprising a region for accommodating at least a part of a body of a user and defining an exterior of the massage device;
a massage module providing a massage function to the part of the body of the user accommodated in the region of the body structure;
a storage unit comprising:
a massage pattern information storage unit storing information about a massage pattern operable by the massage module; and
an audio information storage unit storing information about a sound and a binaural beat provided to the user; and
a control unit comprising:
a massage pattern analysis unit configured to analyze the information about the massage pattern to generate massage pattern analysis information, wherein the massage pattern analysis information includes time data of the massage pattern;
an audio analysis unit configured to analyze the sound provided to the user to generate sound analysis information, wherein the sound analysis information includes time data of the sound; and
an audio optimization unit configured to analyze the time data of the massage pattern analysis information and the time data of the sound analysis information, determine one or more time points at which at least one of the massage pattern or the sound is changed, and change a volume of the sound and a frequency of the binaural beat at the determined one or more time points.

2. The massage device of claim 1, wherein the control unit further comprises an audio mixing unit configured to generate audio information to be provided to the user by mixing the binaural beat and the sound which are changed by the audio optimization unit over time.

3. The massage device of claim 1, wherein the information about the massage pattern or the massage pattern analysis information includes massage step identification information for identifying each of a plurality of massage steps determined based on a massage mode input from the user, and
the massage step identification information includes the time data about the each of the plurality of massage steps.

4. The massage device of claim 3, wherein the audio optimization unit determines a time point at which a previous massage step is changed to a next massage step in the plurality of massage steps based on the time data of the massage step identification information and changes the volume of the sound and the frequency of the binaural beat at the time point at which the previous massage step is changed.

5. The massage device of claim 4, wherein, when the massage mode input from the user is a concentration mode, a first step of the plurality of massage steps comprises changing a state of the user from an arousal state to a stable state, and a last step of the plurality of massage steps comprises changing the state of the user from the stable state to the arousal state.

6. The massage device of claim 1, wherein the information about the massage pattern or the massage pattern analysis information includes massage type identification information for identifying a plurality of massage types which include at least one of tapping, kneading, and acupressure determined based on a massage mode input from the user, and
the massage type identification information includes the time data about the plurality of massage types.

7. The massage device of claim 6, wherein the audio optimization unit determines a time point at which the massage type is changed in the plurality of massage types implemented by the massage module based on the time data and changes the volume of the sound and the frequency of the binaural beat at the time point at which the massage type is changed.

8. The massage device of claim 1, further comprising:
an input unit receiving input from the user of the massage device; and
a display displaying massage mode screen information indicating a massage mode selected by the user of the massage device,
wherein the control controls one or more operations of the massage device based at least in part on the input received by the input unit, and
wherein the massage mode screen information comprises:
an auto mode graphic object associated with a function of executing an auto mode including a predetermined massage pattern and massage time;
a manual mode graphic object associated with a function of executing a manual mode allowing the user of the massage device to set the massage pattern and the massage time; and
a massage option mode graphic object associated with a function of selecting a massage option mode including an additional function of finely adjusting the predetermined massage pattern of the massage device.

9. The massage device of claim 1, wherein the massage pattern information storage unit stores a degree of the change in the volume of the sound and a degree of the change in the frequency of the binaural beat for the changes in massage pattern or in the sound.

10. The massage device of claim 9, wherein the degree of the change in the volume of the sound and the degree of the change in the frequency of the binaural beat for the changed massage pattern or the sound is determined by comparing a scoring value of the volume of the sound and a scoring value of the frequency of the binaural beat prior to the time point at which the massage pattern or the sound is changed with a scoring value of the volume of the sound and a scoring value of the frequency of the binaural beat after the time point, and
wherein the audio optimization unit implements the determined degree of the change in the volume of the sound and the degree of the change in the frequency of the binaural beat at the time point of the change.

* * * * *